US009445988B2

(12) United States Patent
Pertile et al.

(10) Patent No.: US 9,445,988 B2
(45) Date of Patent: Sep. 20, 2016

(54) **EXTRACTS OF *TETRASELMIS* SP**

(75) Inventors: Paolo Pertile, San Pietro Viminario (IT); Lorenzo Zanella, Venezia-Mestre (IT); Martina Herrmann, Hameln (DE); Holger Joppe, Dassel (DE); Sandra Gaebler, Höxter (DE)

(73) Assignee: Symrise AG, Holzminden (DE)

( * ) Notice: Subject to any disclaimer, the term of this patent is extended or adjusted under 35 U.S.C. 154(b) by 1876 days.

(21) Appl. No.: 12/629,441

(22) Filed: Dec. 2, 2009

(65) Prior Publication Data
US 2010/0143267 A1    Jun. 10, 2010

Related U.S. Application Data

(60) Provisional application No. 61/193,537, filed on Dec. 5, 2008.

(51) Int. Cl.
| | |
|---|---|
| A61K 8/97 | (2006.01) |
| A23L 1/30 | (2006.01) |
| A23L 2/52 | (2006.01) |
| A61K 8/02 | (2006.01) |
| A61K 36/05 | (2006.01) |
| A61Q 5/08 | (2006.01) |
| A61Q 7/02 | (2006.01) |
| A61Q 19/02 | (2006.01) |
| A61Q 5/00 | (2006.01) |
| A61Q 5/06 | (2006.01) |
| A61Q 5/10 | (2006.01) |
| A61Q 5/12 | (2006.01) |
| A61Q 9/02 | (2006.01) |
| A61Q 15/00 | (2006.01) |
| A61Q 17/04 | (2006.01) |
| A61Q 19/00 | (2006.01) |
| A61Q 19/04 | (2006.01) |

(52) U.S. Cl.
CPC .............. *A61K 8/975* (2013.01); *A23L 1/3002* (2013.01); *A23L 2/52* (2013.01); *A61K 8/0216* (2013.01); *A61K 36/05* (2013.01); *A61Q 5/08* (2013.01); *A61Q 7/02* (2013.01); *A61Q 19/02* (2013.01); *A61K 2800/92* (2013.01); *A61Q 5/006* (2013.01); *A61Q 5/06* (2013.01); *A61Q 5/065* (2013.01); *A61Q 5/10* (2013.01); *A61Q 5/12* (2013.01); *A61Q 9/02* (2013.01); *A61Q 15/00* (2013.01); *A61Q 17/04* (2013.01); *A61Q 19/002* (2013.01); *A61Q 19/007* (2013.01); *A61Q 19/04* (2013.01)

(58) Field of Classification Search
None
See application file for complete search history.

(56) References Cited

U.S. PATENT DOCUMENTS

| | | | |
|---|---|---|---|
| 4,110,430 A | 8/1978 | Hopp et al. | |
| 4,251,195 A | 2/1981 | Suzuki et al. | |
| 6,214,376 B1 | 4/2001 | Gennadios | |
| 2004/0175782 A1* | 9/2004 | Kravit | 435/41 |
| 2006/0089413 A1 | 4/2006 | Schmaus et al. | |
| 2008/0070825 A1 | 3/2008 | Bertram et al. | |

FOREIGN PATENT DOCUMENTS

| | | |
|---|---|---|
| DE | 4447361 A1 | 6/1996 |
| DE | 10143434 A1 | 3/2003 |
| DE | 10330697 A1 | 2/2005 |
| EP | 0389700 A1 | 10/1990 |
| EP | 0553884 A1 | 8/1993 |
| EP | 0584178 A1 | 3/1994 |
| EP | 0671161 A1 | 9/1995 |
| EP | 1157687 A2 | 11/2001 |
| EP | 1239813 A2 | 9/2002 |
| FR | 2657012 A1 | 7/1991 |
| JP | 7196478 A | 8/1995 |
| JP | 2001354518 A | 12/2001 |
| JP | 2002047145 A * | 12/2002 |
| WO | WO-9415923 A2 | 7/1994 |
| WO | WO-0176572 A2 | 10/2001 |
| WO | WO-0215868 A2 | 2/2002 |
| WO | WO-0238537 A1 | 5/2002 |
| WO | WO-03055587 A1 | 7/2003 |
| WO | WO-2004050069 A1 | 6/2004 |
| WO | WO-2005032501 A1 | 4/2005 |
| WO | WO-2005102252 A2 | 11/2005 |
| WO | WO-2005107692 A1 | 11/2005 |
| WO | WO-2005123101 A1 | 12/2005 |
| WO | WO-2006010661 A1 | 2/2006 |
| WO | WO-2006015954 A1 | 2/2006 |
| WO | WO-2006045760 A1 | 5/2006 |
| WO | WO-2006053912 A1 | 5/2006 |
| WO | WO-2007042472 A1 | 4/2007 |
| WO | WO-2007077541 A2 | 7/2007 |
| WO | WO-2007110415 A2 | 10/2007 |
| WO | WO-2007129331 A2 | 11/2007 |

(Continued)

OTHER PUBLICATIONS

Carballo-Cardenas et al., Vitamin E (Alpha-tocopherol) production by the marine microalgae Dunaliella tertiolecta and Tetraselmis suecica in bath cultivation, 2003, Biomolecular Engineering, 20: 139-147.*

(Continued)

*Primary Examiner* — Terry A McKelvey
*Assistant Examiner* — Catheryne Chen
(74) *Attorney, Agent, or Firm* — Dilworth & Barrese, LLP

(57) ABSTRACT

The present invention relates to extracts of *Tetraselmis* sp., preferably *Tetraselmis suecica*, its cosmetic, dermatological and/or therapeutic uses and compositions and cosmetic, dermatological or therapeutic products comprising such an extract of *Tetraselmis* sp., preferably *Tetraselmis suecica*.

21 Claims, No Drawings

(56) References Cited

FOREIGN PATENT DOCUMENTS

| | | |
|---|---|---|
| WO | WO-2008046676 A1 | 4/2008 |
| WO | WO-2008046795 A1 | 4/2008 |

OTHER PUBLICATIONS

Albuquerque Junior et al., Removal of Cyanobacteria Toxins from Drinking Water by Adsorption on Activated Carbon Fibers, 2008, Materials Research, 11: 371-380.*

* cited by examiner

EXTRACTS OF *TETRASELMIS* SP

CROSS-REFERENCE TO RELATED APPLICATION

This application claims benefit of priority to U.S. Provisional Patent Application No. 61/193,537, filed on Dec. 5, 2008, which is incorporated herein by reference in its entirety.

The present invention relates to extracts of *Tetraselmis* sp., preferably *Tetraselmis suecica*, its cosmetic, dermatological and/or therapeutic uses and compositions and cosmetic, dermatological or therapeutic products comprising such an extract of *Tetraselmis* sp., preferably *Tetraselmis suecica*.

In the field of cosmetic and dermatology, there exists a need to provide agents for influencing or modifying the growth of human hair, i.e. to provide agents for reducing the speed of growth of human hair and/or for un-hairing are sought. Preferably, the influencing or modifying of the growth of human hair should be locally confinable.

On the other hand, in the field of cosmetics there are sought agents for influencing or modifying pigmentation of human skin and/or hair, i.e. agents for increasing coloration of human skin and/or hair (hereinafter also called "browning" or "tanning") or for decreasing pigmentation of the skin and/or hair (hereinafter also called "lightening").

Furthermore, in the field of cosmetic and dermatology, agents for enhancing the epidermal level of protein components of the cornified envelope such as filaggrin and/or involucrin, i.e. to maintain the epidermal texture and skin barrier function or to provide agents with moisturizing or moisture retaining properties are sought.

Hair growth is not a continuous, steadily ongoing procedure, but instead results from the production of hair material in hair follicles that undergo several stages of a hair growth cycle. During a rest phase of the hair follicle, no significant amount of hair material is produced, while during a hair production phase the production of hair material is started or continued.

Sometimes, it is desirable to unhair parts of a human body. Thus, it is for example generally preferred to have hair on the scalp but very often hair is unwanted on other parts of the body, especially on the legs, under the arms and on the face. Furthermore there are pathological hair growth disorders (e.g. hirsutism, folliculitis, pseudofolliculitis barbea) that require medical treatment.

Various procedures have been employed to remove unwanted hair, including shaving, electrolysis, depilatory creams or lotions, waxing, plucking, and therapeutic anti-androgens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring.

Depilatory creams, though very effective, typically are not recommended for frequent use due to their high irritancy potential. Waxing and plucking can cause pain, discomfort, and poor removal of short hair. Finally, antiandrogens, which have been used to treat female hirsutism, can have unwanted side effects.

Skin- or hair-lightening active ingredients intervene in one form or another in melanin metabolism or catabolism. Melanin pigments, which are normally brown to black in colour, are formed in the melanocytes of the skin, transferred to the keratinocytes and give the skin or hair its colour. In mammals, the brown-black eumelanins are primarily formed from hydroxy-substituted aromatic amino acids such as L-tyrosine and L-DOPA, the yellow to red pheomelanins additionally from sulfur-containing molecules (Cosmetics & Toiletries 1996, 111 (5), 43-51). Starting from L-tyrosine, L-3,4-dihydroxyphenylalanine (L-DOPA) is formed by the copper-containing key enzyme tyrosinase and is in turn converted by tyrosinase to dopachrome. By a series of steps catalysed by various enzymes, the latter is oxidised to form melanin.

Skin-lightening agents are used for various reasons: if for some reason the melanin-forming melanocytes in human skin are not evenly distributed, pigment spots occur which are either lighter or darker than the surrounding skin area. To overcome this problem, skin and hair lightening agents are sold which at least partially help to balance out such pigment spots. In addition, many people have a need to lighten their naturally dark skin colour or to prevent skin pigmentation. Hair-lightening agents are useful to lighten regrowing unwanted hair and make it thus less noticeable. In addition, many people have the desire to lighten their naturally dark hair colour. This requires very safe and effective skin and hair lightening agents. Many skin and hair lightening agents contain more or less powerful tyrosinase inhibitors. This is only one possible route towards skin and hair lightening, however.

Furthermore, UV-absorbing substances are also used to protect against the increase in skin pigmentation caused by UV light. This is a purely physically induced effect, however, and must be distinguished from the biological action of skin-lightening agents on cellular melanin formation, which can also be detected in the absence of UV light. Moreover, UV absorbers do not bring about a true lightening of the skin but merely inhibit the increase in skin pigmentation caused by UV light.

Hydroquinone, hydroquinone derivatives such as e.g. arbutin, vitamin C, derivatives of ascorbic acid such as e.g. ascorbyl palmitate, kojic acid and derivatives of kojic acid such as e.g. kojic acid dipalmitate, are used in particular in commercial cosmetic or therapeutic skin and hair lightening formulations.

One of the most commonly used skin and hair lighteners is hydroquinone. However, this compound has a cytotoxic effect on melanocytes and is irritating to the skin. For that reason such preparations are no longer authorised for cosmetic applications in Europe, Japan and South Africa, for example. In addition, hydroquinone is very sensitive to oxidation and can be stabilised only with difficulty in cosmetic formulations. Arbutin is a hydroquinone glucoside, which hydrolyses in situ to form hydroquinone and is therefore just as questionable in toxicological terms as hydroquinone.

Vitamin C and ascorbic acid derivatives have only an inadequate effect on the skin. Furthermore, they do not act directly as tyrosinase inhibitors but instead reduce the coloured intermediate stages of melanin biosynthesis. Kojic acid (5-hydroxy-2-hydroxymethyl-4-pyranone) is a tyrosinase inhibitor which inhibits its catalytic action by chelating the copper atoms in the enzyme; it is used in commercial skin and hair lightening agents but has a high sensitising potential and causes contact allergies.

On the other hand, it is sometimes desirable to tan parts of the body. Skin and hair browning agents can at least partially help to balance out pigment spots if the melanin-forming melanocytes are not evenly distributed. In addition, many people need to tint their naturally pale skin colour and to develop skin pigmentation without being exposed to solar radiation. In addition, some people have the desire to obtain a more intense and homogeneous hair colour. For this reason very safe and effective skin and hair browning agents are necessary.

It is also known that in fair-skinned people high exposure to the sun can cause the breakdown of the vitally important B vitamin folic acid. Folic acid deficiency in pregnancy for example leads to severe deformities. Folic acid is also necessary for DNA synthesis and is therefore essential for sperm production. Folic acid deficiency can therefore lead to infertility. A protection against UV radiation accordingly prevents folic acid deficiency.

Artificial skin browning can be carried out cosmetically or medically, the following main approaches playing a part:

If carotene preparations are taken regularly, carotene is stored in the fatty tissue of the subcutis and the skin gradually turns orange to yellow-brown.

Washable makeup preparations can be used to achieve a light skin tinting (e.g. extracts of fresh green walnut shells, henna).

Skin browning can also be achieved by chemical changes to the skin's stratum corneum using so-called self-tanning preparations. The most important active ingredient is dihydroxyacetone. The skin browning achieved in this way does not wash off and is only removed with the normal flaking of the skin (after around 5 to 10 days). Dihydroxyacetone can be classed as a ketotriose and as a reducing sugar it reacts with the amino acids in the skin or the free amino and imino groups in keratin via a series of intermediate steps along the lines of a Maillard reaction to form brown-coloured substances known as melanoids, which are occasionally also called melanoidins.

One disadvantage of this is that unlike "sun-tanned" skin, the skin browning obtained with dihydroxyacetone does not protect the skin against sunburn. A further disadvantage of dihydroxyacetone lies in the fact that, particularly under the influence of ultraviolet radiation, it releases formaldehyde, albeit usually in small amounts. Dihydroxyacetone also has an unpleasant, chemical odour.

The tint obtained with self-tanning agents is achieved without exposure to sunlight. In contrast, so-called "pre-tan products" or "tan promoters" are also available, which have to be applied before exposure to sunlight. In the sun these preparations then turn yellow, giving rise to a light brown-yellow colouring of the epidermis which further boosts the "suntan".

Another type of artificial browning which is not dependent on UV light can be brought about through the hormones which are usually also released in the body as a consequence of (natural) UV irradiation and ultimately stimulate the melanocytes to synthesise melanin. Examples which can be cited in this connection are derivatives of proopiomelanocortin (POMC) such as [alpha]-MSH (Melanocyte Stimulating Hormone) and synthetic variants (such as [Nle(4), D-Phe(7)]-[alpha]-MSH), which in some cases display far higher activity levels than the natural [alpha]-MSH. Although these hormones can cause browning in principle, their use in cosmetics is prohibited, since they are pharmacologically potent substances (hormones) which should not be widely used without medical indications. There exists thus in the art an ongoing need to provide further agents for influencing or modifying growth of human hair and/or pigmentation of human skin and/or hair.

The epidermis functions as a barrier to limit transepidermal water loss and to protect from the outside environment. The outermost layer of the epidermis, also known as cornified envelope (CE) or horny layer, consists of proteins and lipids. The CE has essential functions, basically represented by mechanical protection, tissue moisture preservation and prevention from the intrusion of allergens and pathogens.

The proteins of the CE are produced by keratinocytes sitting in the upper layer of the epidermis. Keratinocytes are characterized by two fundamental metabolic phases: the proliferative stage, occurring in the cell lines proximal to the basal lamina, followed by an intense activity of synthesis and extracellular deposition of the horny layer proteins. This process induces a progressive cell differentiation, at the end of which the keratinocyte is transformed into an unviable and fully cornified cell (corneocyte), which is coupled with a progressive movement of the cell layer toward the epidermal surface.

Several proteins are involved in the progressive differentiation of keratinocytes. Involucrin and cystatin-alpha are early expressed and deposited directly to the protein scaffold beneath the cell membrane. This first sclerification is enforced by inner (cytoplasmic side) deposition of elafin, small proline-rich proteins (SPRs) and loricrin. This layer is connected to filaments of keratin tied to each other by filaggrin molecules. Finally, the third layer of the CE is deposed and basically represented by abundant loricrin cemented by SPRs. The final composition of the CE is grossly constituted by 2% of involucrin, 5% of cystatin-alpha, 5% of SPRs, 70% of loricrin, 8% of filaggrin, 2% of trichohyaline, 2% of keratin filaments, and 6% of elafin (cystein rich protein).

The expression of these proteins occurs respecting a qualitative and quantitative balance, as a chronological sequence. This is very important in order to assure its biological properties and functions. Involucrin for example, in addition to acting as a scaffolding protein for assembly of early and late expressed CE components, also acts as scaffold to which lipids (predominantly ceramides, but also cholesterol esters and free fatty acids) are covalently attached. Filaggrin controls the shape of keratinocytes, causing aggregation of keratin filaments, which maintains epidermal texture, and it is the source of 70% of the amino acids in the stratum corneum, which maintain epidermal osmolarity and flexibility.

Several skin pathologies are due to structural abnormalities of the proteins participating to the keratinisation process or to their quantitative deficiency. Thus, vulgar psoriasis, for example, is characterized by under-expressed filaggrin, while involucrin is over-expressed. In ichtyosis, filaggrin is under-expressed or absent. In some forms of atopic dermatitis, a multi-factorial syndrome which affects 15-20% of children in developed nations, the biological functionality of the filaggrin is reduced in reason of genetic mutations.

Apart from the pathological pictures, the positive modulation of some proteins playing key-roles in the CE assemblage can appreciably improve the skin wellbeing, basically increasing the moisture content of the tissue.

According to the invention, there is thus provided a method of obtaining a composition for influencing or modifying a) growth of human hair and/or
b) pigmentation of human skin and/or hair
c) epidermal level of CE protein components such as filaggrin and/or involucrin, comprising the step of extracting substantially intact cells of *Tetraselmis* sp., preferably *Tetraselmis suecica*, with a liquid extractant selected from the group consisting of hexane, ethyl acetate, ethanol, water, methanol, isopropanol and mixtures of two or more of these extractants,
wherein the extraction comprises a) exposition of the cell material to the extractant for up to 24 h at a temperature of not more than 50° C., and b) removal of the cell material to obtain an extract, the extract being the composition or being further processed into the composition.

For the purposes of this invention, cells are considered substantially intact when they are viable, dried or freeze-dried. The cells are not homogenized, sonicated or milled or otherwise subjected to substantial disintegration.

In contrast to the present invention, FR 2657012 discloses in example 3 an extract from Tetraselmis algae obtained by introducing the algae in aqueous ethanol (water:ethanol=9:1 (v/v)) and disintegrating said algae with a mixer having high shear forces (ultra turrax). Subsequently the extraction was carried out for 24 h at ambient temperature. The disrupted algae were separated off by filtration. Such disrupted, substantially disintegrated algae are not used according to the present invention.

Jearrousse et al. (Arch. Dermatol. Res. 2007, 299, 441-447) performed advanced research on the expression of CE proteins and pointed out that filaggrin and integrins can be modulated by treatment with natural extracts obtained from cultures of Propionibacterium acnes, a bacterium identified among the etiologic causes of the acne vulgaris.

Compounds active on filaggrin level modulation have been marketed by Pierre Fabre S.A. with the trade name dexamine; a product used to reduce the dryness of skin both in cosmetics and in medicine (i.e. by treating ichtyosis).

Stimulant activities on both filaggrin and involucrin have been disclosed also by using extracts obtained from cyanobacteria and microalgae living in saline hot waters (WO2007129331).

A significant stimulation of the horny layer proteins has been also detected by using extracts obtained from the well-known cyanobacterium Arthrospira, commonly named Spirulina (EP1239813).

Extracts obtainable from macroalgae have also been resulted exploitable for the modulation of the keratinization processes, as disclosed by Lion Corp. (JP2001354518; JP2001131049) for several genera.

It is generally known that different biological species comprise different substances. Thus, effects obtainable by use of one microalgal species cannot be used to predict the effects obtainable by use of a different microalgal species. Furthermore, as will be shown hereinafter, the effects obtainable by extracts of Tetraselmis sp., preferably Tetraselmis suecica, depend on the exact extraction conditions and may even be reversed upon modification of the extractant and extraction method.

It was thus surprising that the extracts of Tetraselmis sp., preferably Tetraselmis suecica, as obtained according to the invention are useful for influencing or modifying growth of human hair and/or pigmentation of human skin and/or hair and/or stimulating the level of CE protein components such as filaggrin and involucrin. Also, the extracts of the present invention favourably allow the production of effective compositions by simple and reliable methods starting from biological materials, i.e. microalgal cell material.

Tetraselmis suecica algae have been cultured in Italy for some time, e.g. cultured by an Italian hatchery in Orbetello. Furthermore, six strains of Tetraselmis suecica of different origin are available from CCAP (Culture Collection of Algae and Protozoa), e.g. CCAP 66/4, CCAP 66/22A, CCAP 66/22B, CCAP 66/22C, CCAP 66/22D and CCAP 66/38 (http://www.ccap.ac.uk/results.php?mode=basic&strainsearch=tetraselmis+suecica).

According to the present invention, cell material of Tetraselmis sp., preferably Tetraselmis suecica, is extracted with a liquid extractant selected from the group consisting of hexane, ethyl acetate, ethanol, water, methanol, isopropanol. The extractant can also be a mixture of two or more of the aforementioned extractants. These extractants have provided best results for influencing or modifying growth of human hair and/or pigmentation of human skin and/or hair and/or epidermal level of CE protein components such as filaggrin and/or involucrin.

For extraction, the cell material is in step a) contacted with the liquid extractant for up to 24 h at a temperature of not more than 50° C., preferably at a temperature of 16-40° C. and most preferably at a temperature of 20-30° C. Also, exposition of the cell material to the extractant preferably lasts for up to 24 h, more preferably for 1-10 h and most preferably for 2-6 h. For all extraction conditions described herein, best results have been achieved when the extraction was performed in the dark. Also, during contact of the cell material with the extractant the material is preferably agitated, preferably by stirring.

Preferably, the ratio (w:v) of dry cell material to liquid extractant is 200 mg:1 ml to 1 mg:1 ml, more preferably 140 mg:1 ml to 5 mg:1 ml, and most preferably 80 mg:1 ml to 10 mg:1 ml when using freeze-dried cell material as detailed below.

In step b) an extract is obtained by removal of the cell material, preferably by centrifugation, filtration or decantation or other suitable methods. A particle-free supernatant according to visual inspection is thus obtained, typically of green colour. The extract can be used as a composition for influencing or modifying growth of human hair and/or pigmentation of human skin and/or hair and/or epidermal level of CE protein components such as filaggrin and involucrin, or, more preferably, is further processed into such composition as detailed below.

The cell material removed from the extract in step b) can be used for another exposition to the extractant in step a), typically for a few minutes, preferably up to 1 h. The extraction thus preferably comprises repeating steps a) and b) once, twice, three or four times, preferably once or twice, and in each step a) the cell material removed in the respective prior step b) is used, and the extracts of steps b) are combined. This way, a continued extract with reproducible composition and high yield of extracted active ingredients can be obtained.

In a preferred method according to the present invention, the cell material used in a step a) of the extraction is obtained in step b) of a prior extraction with a different extractant. Thus, two extracts or compositions are provided, and the method can be repeated to provide further extracts or compositions.

Particularly preferred are extracts and compositions obtainable or obtained by any of the following extractions:
1. Extraction with ethyl acetate, followed by extraction with ethanol, followed by extraction with water or extraction with ethyl acetate followed by extraction with 30% aqueous ethanol or with water
2. Extraction with methanol, ethanol or isopropanol, followed by extraction with water
3. Extraction with hexane, followed by extraction with ethyl acetate, followed by extraction with ethanol, followed by extraction with water.

The phototoxicity of the extracts and composition is preferably adjusted to a phototoxicity index of less than 5 according to the Official Journal of the European Communities, directive 2000/33/EG of the commission from Apr. 25, 2000, appendix II, B.41 and the OECD Guideline 432. At a phototoxicity index of less than 5, the composition is no longer considered to possess phototoxic potential.

For adjusting phototoxicity the optionally combined extract—not in solid form—is preferably treated with activated carbon in a ratio dry extract:activated carbon of 3:1 to 1:30 (w/w), preferably 1:1 to 1:15 (w/w). The term 'dry extract' according to the present invention refers to the extractant-free weight of an extract according to the present invention, e.g. as obtainable by completely removing the extractant. This treatment may result in a minor loss of activity for influencing or modifying the growth of human hair and/or pigmentation of human skin and/or hair. However, the treatment reliably removes phototoxic ingredients otherwise comprised in the extract. A further benefit of this treatment is a colour reduction of most of the extracts.

For preparing the composition, the extractant is preferably removed from the—optionally combined—extract, preferably by evaporation or other suitable processes, to obtain the extract in concentrated or dry form (dry extract), the latter preferably as a suspension, a viscous liquid, a powder or as granules. The concentrated form preferably contains 50-80 wt. % dry matter and 50-20 wt. % residual extractant.

The composition is then formed by optionally adding a cosmetically and/or dermatologically and/or therapeutically acceptable solid carrier to the extract in concentrated or dry form (dry extract) and then optionally drying the mixture by suitable processes. In this context, such a solid which is at least not toxic to the organisms on which it is to be used is cosmetically, dermatologically or therapeutically acceptable. Preferred solids are hydrocolloids such as starches, degraded or chemically or physically modified starches (in particular dextrins and maltodextrin), lactose, modified celluloses, gum arabic, gum ghatti, tragacanth gum, karaya, carrageenan, pullulan, curdlan, xanthan gum, gellan gum, guar gum, locust bean gum, alginates, agar, pectin, inulin or glucose and mixtures of two or more of these solids.

The composition can also be formed by optionally adding a cosmetically and/or dermatologically and/or therapeutically acceptable solvent, such as e.g. neutral oil, mineral oil, silicone oil, plant oils, triglycerides, fatty alcohols, fatty acid esters, polyol fatty acid esters such as PEG-7 glyceryl cocoate available e.g. as Cetiol HE from Cognis, ethanol, 1,2-propylene glycol, 1,3-butylene glycol, dipropyleneglycol, triethyl citrate, 1,2-pentanediol or other 1,2-alkanediols, glycerin and water and mixtures of two or more of these solvents to the extract in concentrated or dry form (dry extract) and optionally completely removing the residual extractant by a suitable process. Such compositions prepared according to the invention are readily further processable in particular for cosmetic purposes. These compositions can optionally be prepared with the addition of a solubilizing agent, preservative or antioxidant.

Most preferably, the solvent comprises, consist essentially of or is selected from the 1,2-diols 1,2-pentanediol, 1,2-hexanediol or mixtures thereof, and optionally further comprises one or more of the aforementioned solvents, preferably water. The diols not only possess very good solubilizing properties but exhibit also bioavailability enhancing and moisturizing activity. Furthermore, depending on the concentration of the 1,2-diols no further preservation or only reduced levels of preservatives are needed to protect the composition from microbial growth. Antioxidants such as for example tocopherol or tocopherol mixtures, tocopherol acetate, BHT or other suitable antioxidants are also easily incorporated.

For very lipophilic extracts such as for example hexane or ethyl acetate extracts, preferred solvent comprise, consists of or are selected from neutral oil, mineral oil, silicone oil, plant oils, triglycerides, fatty alcohols, fatty acid esters, polyol fatty acid esters, dipropyleneglycol, triethyl citrate and ethanol, and mixtures of two or more of these.

The extract or the liquid or solid composition comprising the extract can furthermore also be further processed by encapsulation with a solid shell material, which is preferably chosen from starches, degraded or chemically or physically modified starches (in particular dextrins and maltodextrins), gelatines, wax materials, liposomes, gum arabic, agar-agar, ghatti gum, gellan gum, modified and non-modified celluloses, pullulan, curdlan, carrageenans, algic acid, alginates, pectin, inulin, xanthan gum and mixtures of two or more of the substances mentioned.

The solid shell material is preferably selected from gelatine (pork, beef, poultry and/or fish gelatines and mixtures thereof are advantageous, preferably including at least one gelatine having a Bloom value of greater than or equal to 200, preferably having a Bloom value of greater than or equal to 240), maltodextrin (preferably obtained from maize, wheat, tapioca or potato, preferred maltodextrins displaying a DE value in the range from 10 to 20), modified cellulose (e.g. cellulose ether), alginates (e.g. Na alginate), carrageenan (beta-, iota-, lambda- and/or kappa-carrageenan), gum arabic, curdlan and/or agar-agar. Gelatine is used in particular because of its good availability in various Bloom values. Production can take place as described for example in EP 0 389 700 A, JP 7 196 478, U.S. Pat. No. 4,251,195, U.S. Pat. No. 6,214,376, WO 03/055587 or WO 2004/050069.

The compositions in liquid, solid (not the dry extract) or encapsulated form obtainable or obtained according to the present invention comprise 0.001 to 20 wt. %, preferably 0.01 to 10 wt % and most preferably 0.1-5 wt % dry extract of the total composition.

According to the invention, a composition for inhibiting growth of human hair and decreasing pigmentation of human skin and/or hair is provided, which is produced according to a method according to the invention as described above, and wherein the composition is or comprises an extract obtained by using hexane, ethyl acetate, methanol or ethanol as extractant or a mixture of any of these extractants. It has surprisingly been found that by extracting *Tetraselmis* sp., preferably *Tetraselmis suecica*, cell material, particularly freeze-dried material, with (first extraction) hexane, ethyl acetate, methanol or ethanol or with ethyl acetate, followed by (second) extraction with 30% aqueous ethanol or with hexane, followed by (second) extraction with ethyl acetate, followed by (third) extraction with ethanol, the aforementioned effects can be achieved.

For inhibiting growth of human hair while increasing pigmentation of human skin and/or hair, a composition is provided according to the invention that is or comprises an extract obtained by using iso-propanol or water. It has surprisingly been found that by extracting *Tetraselmis* sp., preferably *Tetraselmis suecica*, cell material with water, preferably after prior extraction of freeze-dried material with methanol, ethanol, ethyl acetate and/or hexane, the aforementioned effects can be achieved.

For stimulating the epidermal level of CE protein components such as filaggrin and/or involucrin, a composition is provided according to the invention that is or comprises an extract obtained by using ethyl acetate, methanol, ethanol or water as extractant or a mixture of any of these extractants. It has surprisingly been found that by extracting *Tetraselmis* sp., preferably *Tetraselmis suecica*, cell material, particularly freeze-dried material, with ethyl acetate, methanol, ethanol or water or with ethylacetate, followed by extraction with ethanol or methanol, followed by extraction with water or with ethanol or methanol, followed by extraction with water, the aforementioned effects can be achieved.

The composition of the present invention can favourably be part of a cosmetic, dermatologic or therapeutic product. In such product the composition is preferably present in an amount sufficient to achieve the aforementioned effects upon application of the product to the human skin and/or hair or after oral consumption.

The concentration of the composition in a cosmetic, dermatological or therapeutic product (for topical or oral application) preferably is
  at least 0.001 ppm, preferably at least and 0.01 ppm and most preferably at least 0.1 ppm, and
  at most 500 ppm, preferably at most 200 ppm and most preferably at most 50 ppm
dry extract of the total product.

The cosmetic, dermatological or therapeutic products according to the invention are produced by conventional processes known per se, such that the extract or the extract composition is incorporated into cosmetic, dermatological or therapeutic products which can have a conventional composition and which in addition to the aforementioned effects can also be used for the treatment, care and cleansing of the skin or hair.

Essential fields of use for extracts or extract compositions according to the invention are cosmetic, dermatological or therapeutic products which (apart from the presence of the extract according to the invention) serve for cosmetic or dermatological light protection, for treatment, care and cleansing of the skin and/or hair or as a make-up product in decorative cosmetics. Such products can accordingly be present e.g. as a cleansing composition, such as e.g. soap, syndet, liquid washing, shower and bath preparation, skin care composition, such as e.g. emulsion (as a solution, dispersion, suspension; cream, lotion or milk of the W/O, O/W or multiple emulsion, PIT emulsion, emulsion foam, micro- or nanoemulsion, Pickering emulsion type, depending on the preparation process and constituents), ointment, paste, gel (including hydro-, hydrodispersion-, oleogel), alcoholic or aqueous/alcoholic solution, oil, toner, balsam, serum, powder (e.g. face powder, body powder), soaking liquid for wipes, Eau de Toilette, Eau de Cologne, perfume, wax, including the presentation form as a mask, mousse, stick, pencil, roll-on, (pump) spray, aerosol (foaming, non-foaming or after-foaming), skin care composition (as described above) as a foot care composition (including keratolytics, deodorant), as an insect repellent composition, as a sunscreen composition, as a self-tanning composition and/or aftersun preparation, skin care composition as a shaving composition or after-shave, as a hair-removing composition, as a hair care composition, such as e.g. shampoo (including shampoo for normal hair, for greasy hair, for dry, stressed (damaged) hair, 2-in-1 shampoo, anti-dandruff shampoo, baby shampoo, shampoo for a dry scalp, shampoo concentrate), conditioner, hair treatment cure, hair tonic, hair lotion, hair rinse, styling cream, pomade, permanent wave and fixing compositions, hair smoothing composition (straightening composition, relaxer), hair setting composition, styling aid (e.g. gel or wax); blonding composition, hair colouring composition, such as e.g. temporary, directly absorbed, semi-permanent hair colouring composition, permanent hair colouring composition), skin care composition as a decorative body care composition, such as e.g. nail care composition (nail varnish and nail varnish remover), decorative cosmetic (e.g. powder, eye shadow, kajal pencil, lipstick, mascara), make-up, make-up remover, skin care composition as a deodorant and/or antiperspirant.

It is also advantageous to administer the extract or extract composition orally e.g. in the form of tablets, dragees, capsules, juices, solutions and granules or in form of orally consumable products used for alimentation which in addition to their function as foodstuff provide beauty from inside.

Compositions according to the present invention can advantageously be combined, in particular in cosmetic products, with further conventional components, such as, for example:
preservatives, in particular those described in US 2006/0089413, antimicrobial agents, such as e.g. antibacterial agents or agents to treat yeast and mold, in particular those described in WO 2005/123101, antiacne and sebum reducing agents, in particular those described in WO 2008/046791, compounds against ageing of the skin, in particular those described in WO 2005/123101, antidandruff agents, in particular those described in WO 2008/046795, antiirritants (antiinflammatory agents, irritation-preventing agents, irritation-inhibiting agents), in particular those described in WO 2007/042472 and US 2006/0089413, antioxidants, in particular those described in WO 2005/123101, carrier materials, in particular those described in WO 2005/123101, chelating agents, in particular those described in WO 2005/123101, deodorizing agents and antiperspirants, in particular those described in WO 2005/123101, moisture regulators (moisture-donating agents, moisturizing substance, moisture-retaining substances), in particular those described in WO 2005/123101, osmolytes, in particular those described in WO 2005/123101, compatible solutes, in particular those described in WO 01/76572 and WO 02/15868, proteins and protein hydrolysates, in particular those described in WO 2005/123101 and WO200846676, skin-lightening agents, in particular those described in WO 2007/110415, skin-tanning agents, in particular those described in WO 2006/045760, cooling agents, in particular those described in WO 2005/123101, skin-cooling agents, in particular those described in WO 2005/123101, warming agents, in particular those described in WO 2005/123101, UV-absorbing agents, in particular those described in WO 2005/123101, UV filters, in particular those described in WO 2005/123101, benzylidene-beta-dicarbonyl compounds in accordance with WO 2005/107692 and alpha-benzoyl-cinnamic acid nitriles in accordance with WO 2006/015954, insect repellents, in particular those described in WO 2005/123101, plant parts, plant extracts, in particular those described in WO 2005/123101, vitamins, in particular those described in WO 2005/123101, emulsifiers, in particular those described in WO 2005/123101, gelling agents, in particular those described in WO 2005/123101, oils in particular those described in WO 2005/123101, waxes in particular those described in WO 2005/123101, fats in particular those described in WO 2005/123101, phospholipids, in particular those described in WO 2005/123101, saturated fatty acids and mono- or polyunsaturated fatty acids and α-hydroxy acids and polyhydroxy-fatty acids and esters of saturated and/or unsaturated branched and/or unbranched alkane carboxylic acids, in particular those described in WO 2005/123101, surface-active substances (surfactants) in particular those described in WO 2005/123101, skin repair agents comprising cholesterol and/or fatty acids and/or ceramides and/or pseudoceramides, in particular those described in WO 2006/053912, dyestuffs and colorants and pigments, in particular those described in WO 2005/123101, aroma chemicals and flavors and fragrances, in particular those described in S. Arctander, Perfume and Flavor Chemicals, private publishing house, Montclair, N.J., 1969 and Surburg, Panten, Common Fragrance and Flavor Materials, 5th Edition, Wiley-VCH, Weinheim 2006, preferably those explicitly mentioned in US 2008/0070825, alcohols and polyols, in particular those described in WO 2005/123101, organic solvents, in particular those described in WO 2005/123101, silicones and silicone oils and silicone derivatives in particular those described in WO2008/046676, virucides, abrasives, anti-cellulite agents, astringents, antiseptic agents, antistatics, binders, buffers, cell stimulants, cleansing agents, care agents, depilatory agents, softeners, enzymes, essential oils, in particular those described in US 2008/0070825, fibres, film-forming agents, fixatives, foam-forming agents, foam stabilizers, substances for preventing foaming, foam boosters, gel-forming agents, hair growth activators, hair growth inhibitors, hair care agents, hair-setting agents, hair-straightening agents, hair-smoothening, bleaching agents, strengthening agents, stain-removing agents, optically brightening agents, impregnating agents, dirt-repellent agents, friction-reducing agents, lubricants, opacifying agents, plasticizing agents, covering agents, polish, gloss agents, polymers in particular those described in WO2008/046676, powders, peptides, mono-, di- and oligosaccharides, re-oiling agents, abrading agents, skin-soothing agents, skin-cleansing agents, skin care agents, skin-healing agents, skin-protecting agents, skin-softening agents, skin-smoothing agents, nourishing agents, skin-warming agents, stabilizers, detergents, fabric conditioning agents, suspending agents, thickeners, yeast extracts, algae or microalgae extracts, animal extracts, liquefiers, color-protecting agents, anticorrosives and electrolytes.

Auxiliary substances and additives can be included in quantities of 5 to 99.99 wt. %, preferably 10 to 80 wt. %, based on the total weight of the product. The amounts of cosmetic or dermatological auxiliary agents and additives and perfume to be used in each case can easily be determined by the person skilled in the art by simple trial and error, depending on the nature of the particular product.

The products can also contain water in a quantity of up to 99.99 wt. %, preferably 5 to 80 wt. %, based on the total weight of the product.

Products according to the invention can contain one or more further hair growth inhibiting agents. A more rapid hair growth reduction based in part on synergistic effects can be achieved in this way.

Agents to inhibit hair growth are for example activin, activin derivatives or activin agonists, ornithine decarboxylase inhibitors such as alpha-difluoromethylomithine or pentacyclic triterpenes like for example ursolic acid, betulin, betulinic acid, oleanolic acid and derivatives thereof, ornithine amino transferase inhibitors, serine proteases, 5alpha-reductase inhibitors, 5-lipoxygenase inhibitors, cyclooxygenase inhibitors, protein-tyrosine kinase inhibitors, protein kinase C inhibitors, sulfotransferase inhibitors, nitric oxide synthetase inhibitors, alkaline phosphatase inhibitors, inhibitors of elastase-like enzymes, neutral endopeptidase inhibitors, matrix metalloproteinase inhibitors, inhibitors of a cysteine pathway enzyme, androgen receptor antagonists, S-adenosylmethionine decarboxylase inhibitors, gamma-glutamyl transpeptidase inhibitors, transglutaminase inhibitors, VEGF modulators, compounds which block the glucose transfer across the membranes of the cells of hair follicles such as phloretin, soybean-derived serine protease inhibitors, extracts from microorganisms, algae, microalgae or plants and plant parts of for example the families Leguminosae, Solanaceae, Graminae, Asclepiadaceae or Cucurbitaceae, the genera *Chondrus, Gloiopeltis, Ceramium, Durvillea, Glycine max, Sanguisorba officinalis, Calendula officinalis, Hamamelis virginiana, Arnica montana, Salix alba, Hypericum perforatum* or *Gymnema sylvestre*.

The amount of the aforementioned examples of additional active ingredients for the modulation of hair growth (one or more compounds) in the formulations according to the invention is then preferably 0.00001 to 30 wt. %, preferably 0.0001 to 20 wt. %, particularly preferably 0.001 to 5 wt. %, based on the total weight of the product.

The products according to the invention can preferably also contain other active ingredients which modulate skin and/or hair pigmentation and which are suitable for cosmetic (e.g. dermatological) and/or therapeutic applications. A more rapid modulation of skin and/or hair pigmentation based in part on synergistic effects can be achieved in this way.

Advantageous skin and hair lightening active ingredients in this respect are kojic acid (5-hydroxy-2-hydroxymethyl-4-pyranone), kojic acid derivatives e.g. kojic acid dipalmitate, arbutin, ascorbic acid, ascorbic acid derivatives, hydroquinone, hydroquinone derivatives, resorcinol, sulfur-containing molecules such as e.g. glutathione or cysteine, alpha-hydroxy acids (e.g. citric acid, lactic acid, malic acid) and derivatives thereof, N-acetyl tyrosine and derivatives, undecenoyl phenylalanine, gluconic acid, 4-alkyl resorcinols, 4-(1-phenylethyl)-1,3-dihydroxybenzene, chromone derivatives such as aloesin, flavonoids, thymol derivatives, 1-aminoethyl phosphinic acid, thiourea derivatives, ellagic acid, nicotinamide (niacinamide), zinc salts such as e.g. zinc chloride or gluconate, thujaplicin and derivatives, triterpenes such as maslinic acid, sterols such as ergosterol, benzofuranones such as senkyunolide, vinyl and ethyl guiacol, dionic acids such as octodecene dionic acid and azelaic acid, inhibitors of nitrogen oxide synthesis, such as e.g. L-nitroarginine and derivatives thereof, 2,7-dinitroindazole or thiocitrulline, metal chelators (e.g. alpha-hydroxy fatty acids, palmitic acid, phytic acid, lactoferrin, humic acid, bile acid, bile extracts, bilirubin, biliverdin, EDTA, EGTA and derivatives thereof), retinoids, soya milk and extract, serine protease inhibitors or lipoic acid or other synthetic or natural active ingredients for skin and hair lightening, the latter also being used in the form of an extract from plants, such as e.g. bear-berry extract, rice extract, papaya extract, liquorice root extract or constituents concentrated therefrom, such as glabridin or licochalcone A, artocarpus extract, extract of *rumex* and *ramulus* species, extracts of pine species (*pinus*) and extracts of *vitis* species or stilbene derivatives concentrated therefrom, extract of saxifrage, mulberry, scutelleria or/and grapes.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophylline and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate (Zn(Gly)2), manganese(II) bicarbonate complexes ("pseudocatalases") as described for example in EP 0 584 178, tetrasubstituted cyclohexene derivatives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and analogues thereof, activators of adenylate cyclase and compounds which activate the transfer of melanosomes to keratinocytes such as serine proteases or agonists of the PAR-2 receptor, extracts of plants and plant parts of the *chrysanthemum* species, *sanguisorba* species, walnut extracts, urucum extracts, rhubarb extracts, trehalose, erythrulose and dihydroxyacetone. Flavonoids which bring about skin and hair tinting or browning (e.g. quercetin, rhamnetin, kaempferol, fisetin, genistein, daidzein, chrysin and apigenin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the preparation.

Products according to the present invention in the form of cosmetic and/or dermatologically active products are applied to the skin and/or hair in a sufficient amount in the conventional manner for cosmetics and dermatics. In this context, cosmetic and dermatological products according to the present invention which additionally act as sunscreen products offer particular advantages. These products (formulations) advantageously comprise at least one UVA filter and/or at least one UVB filter and/or at least one inorganic pigment. In this context, the products can be in various forms such as are conventionally employed e.g. for sunscreen formulations. They can be e.g. a solution, an emulsion of the water-in-oil (W/O) type or of the oil-in-water (O/W) type or a multiple emulsion, for example of the water-in-oil-in-water (W/O/W) type, a gel, a hydrodispersion, a solid stick or also an aerosol.

As mentioned, products according to the present invention can advantageously be combined with substances which absorb UV radiation, the total amount of the filter substances being e.g. 0.01 to 40 wt.-%, preferably 0.1 to 10 wt.-%, in particular 1.0 to 5.0 wt.-%, based on the total weight of the formulations, in order to provide cosmetic products which protect the hair or skin from ultraviolet radiation.

Preferred products of the present invention are sunscreen formulations in the form of aqueous emulsions, preferably of the water-in-oil (W/O) or of the oil-in-water (O/W) type or a multiple emulsion, for example of the water-in-oil-in-water (W/O/W) type, more preferably of the oil-in-water (O/W) type.

Preferred sunscreen formulations (products) of the present invention comprise a total amount of organic UV filters of greater than 10 wt.-%, preferably in the range of from 12 to 40 wt.-%, more preferred in the range of from 15 to 35 wt.-%, based on the total weight of the sunscreen formulation.

In this context advantageous organic UV filters are:
p-aminobenzoic acid
p-aminobenzoic acid ethyl ester (25 mol) ethoxylated
p-dimethylaminobenzoic acid-2-ethylhexyl ester
p-aminobenzoic acid ethyl ester (2 mol) N-propoxylated
p-aminobenzoic acid glycerol ester
salicylic acid homomethyl ester (homosalates) (Neo Heliopan® HMS)
salicylic acid-2-ethylhexyl ester (Neo Heliopan® OS)
triethanolamine salicylate
4-isopropyl benzyl salicylate
anthranilic acid menthyl ester (Neo Heliopan® MA)
diisopropyl cinnamic acid ethyl ester
p-methoxycinnamic acid-2-ethylhexyl ester (Neo Heliopan® AV)
diisopropyl cinnamic acid methyl ester
p-methoxycinnamic acid isoamyl ester (Neo Heliopan® E 1000)
p-methoxycinnamic acid diethanolamine salt
p-methoxycinnamic acid isopropyl ester
2-ethylhexyl-2-cyano-3,3-diphenyl acrylate (Neo Heliopan® 303)
ethyl-2-cyano-3,3'-diphenyl acrylate
2-phenylbenzimidazole sulfonic acid and salts (Neo Heliopan® Hydro)
3-(4'-trimethylammonium)benzylidene bornan-2-one methyl sulfate
terephthalylidene dibornane sulfonic acid and salts (Mexoryl® SX)
4-t-butyl-4'-methoxydibenzoyl methane (avobenzone)/(Neo Heliopan® 357)
β-imidazole-4(5)-acrylic acid (urocanic acid)
2-hydroxy-4-methoxybenzophenone (Neo Heliopan® BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
3-(4'-sulfo)benzylidene bornan-2-one and salts
3-(4'-methyl benzylidene)-d,l-camphor (Neo Heliopan® MBC)
3-benzylidene-d,l-camphor
4-isopropyl dibenzoyl methane
2,4,6-trianilino-(p-carbo-2'-ethylhexyl-1'-oxy)-1,3,5-triazine
phenylene bis-benzimidazyl tetrasulfonic acid disodium salt (Neo Heliopan® AP)
2,2'-(1,4-phenylene)-bis-(1H-benzimidazole-4,6-disulfonic acid), monosodium salt
N-[(2 and 4)-[2-(oxoborn-3-ylidene)methyl]benzyl]acrylamide polymer
phenol, -(2H-benzotriazol-2-yl)-4-methyl-6-(2-methyl-3(1,3,3,3-tetramethyl-1-(trimethylsilyl)oxy)disiloxanyl)propyl), (Mexoryl® XL)
4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb® HEB)
2,2'-methylene bis-(6-(2H-benzotriazol-2-yl)-4-1,1,3,3-tetramethylbutyl)phenol), (Tinosorb® M)
2,4-bis-[4-(2-ethylhexyloxy)-2-hydroxyphenyl]-1,3,5-triazine
benzylidene malonate polysiloxane (Parsol® SLX)
glyceryl ethylhexanoate dimethoxycinnamate
disodium-2,2'-dihydroxy-4,4'-dimethoxy-5,5'-disulfobenzophenone
dipropylene glycol salicylate
sodium hydroxymethoxybenzophenone sulfonate
4,4',4-(1,3,5-triazine-2,4,6-triyltriimino)-tris-benzoic acid tris(2-ethylhexyl ester) (Uvinul® T150)
2,4-bis-[{(4-(2-ethylhexyloxy)-2-hydroxy}phenyl]-6-(4-methoxyphenyl)-1,3,5-triazine (Tinosorb® S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethylhexyloxy)-2-hydroxy}phenyl]-6-[4-(2-methoxyethyl carbonyl)phenylamino]-1,3,5-triazine
2,4-bis-[{4-(3-(2-propyloxy)-2-hydroxypropyloxy)-2-hydroxy}phenyl]-6-[4-(2-ethylcarboxyl)phenylamino]-1,3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2"-methylpropenyloxy)-2-hydroxy}phenyl]-6-(4-methoxyphenyl)-1,3,5-triazine
2,4-bis-[{4-(1',1',1',3'5',5',5'-heptamethylsiloxy-2"-methylpropyloxy)-2-hydroxy}phenyl]-6-(4-methoxyphenyl)-1,3,5-triazine
2-(4-diethylamino-2-hydroxybenzoyl)benzoic acid hexyl ester (Uvinul® A Plus)
indanylidene compounds in accordance with WO 02/38537

Organic UV filters which are particularly preferred in products of the present invention (in particular if they are in the form of a sunscreen formulation), preferably in an amount mentioned (above), are:

p-aminobenzoic acid
3-(4'-trimethylammonium)benzylidene bornan-2-one methyl sulfate
salicylic acid homomethyl ester (Neo Heliopan® HMS)
2-hydroxy-4-methoxybenzophenone (Neo Heliopan® BB)
2-phenylbenzimidazole sulfonic acid (Neo Heliopan® Hydro)
terephthalylidene dibornane sulfonic acid and salts (Mexoryl® SX)
4-tert-butyl-4'-methoxydibenzoyl methane (Neo Heliopan® 357)
3-(4'-sulfo)benzylidene bornan-2-one and salts
2-ethylhexyl-2-cyano-3,3-diphenyl acrylate (Neo Heliopan® 303)
N-[(2 and 4)-[2-(oxoborn-3-ylidene)methyl]benzyl]acrylamide polymer
p-methoxycinnamic acid-2-ethylhexyl ester (Neo Heliopan® AV)
p-aminobenzoic acid ethyl ester (25 mol) ethoxylated
p-methoxycinnamic acid isoamyl ester (Neo Heliopan® E1000)
2,4,6-trianilino-(p-carbo-2'-ethylhexyl-1'-oxy)-1,3,5-triazine (Uvinul® T150)
phenol, 2-(2H-benzotriazol-2-yl)-4-methyl-6-(2-methyl-3 (1,3,3,3-tetramethyl-1-(trimethylsilyl)oxy)disiloxyanyl) propyl), (Mexoryl® XL)
4,4'-[(6-[4-(1,1-dimethyl)aminocarbonyl)phenylamino]-1,3, 5-triazine-2,4-diyl)diimino]-bis-(benzoic acid-2-ethylhexyl ester) (Uvasorb HEB)
3-(4'-methyl benzylidene)-d,l-camphor (Neo Heliopan® MBC)
3-benzylidene camphor
salicylic acid-2-ethylhexyl ester (Neo Heliopan® OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetramethylbutyl)phenol) (Tinosorb® M)
phenylene bis-benzimidazyl tetrasulfonic acid disodium salt (Neo Heliopan® AP)
2,4-bis-[{(4-(2-ethylhexyloxy)-2-hydroxy}phenyl]-6-(4-methoxyphenyl)-1,3,5-triazine, (Tinosorb® S)
benzylidene malonate polysiloxane (Parsol® SLX)
menthyl anthranilate (Neo Heliopan® MA)
2-(4-diethylamino-2-hydroxybenzoyl)benzoic acid hexyl ester (Uvinul® A Plus)
indanylidene compounds in accordance with WO 02/38537

Products according to the present invention in the form of sunscreen formulations preferably have a SPF (sun protection factor) of equal or greater than 15, preferably of equal or greater than 20, more preferably of equal or greater than 30.

Preferred products of the present invention in the form of sunscreen formulations comprise 4-(1,1-dimethylethyl)-4'-methoxydibenzoylmethane (4-t-butyl-4'-methoxydibenzoyl methane; avobenzone), preferably in an amount in the range of from 0.2-10 wt.-%, more preferred in the range of from 0.5-5 wt.-%, based on the total weight of the sunscreen formulation.

In preferred sunscreen formulations comprising components (a) and (b) the pH-value is in the range of from pH 4 to pH 8, preferably from pH 4 to 6.5.

The products according to the invention can preferably also contain other agents which stimulate the level of CE proteins or moisture regulators or osmolytes which also have skin-moistening properties and which are suitable for cosmetic (e.g. dermatological) and/or therapeutic applications. A more rapid moisture regulation of the skin based in part on synergistic effects can be achieved in this way.

Advantageous moisture regulating agents in this respect are sodium lactate, urea, alcohols, sorbitol, glycerol, diols such as propylene glycol, 1,2-pentanediol, 1,2-hexanediol and 1,2-octanediol, collagen, elastin or hyaluronic acid, diacyl adipates, petroleum jelly, ectoine, urocanic acid, lecithin, pantheol, phytanetriol, lycopene, ceramides, cholesterol, glycolipids, chitosan, chondroitin sulfate, polyamino acids and sugars, lanolin, lanolin esters, amino acids, alpha-hydroxy acids (e.g. citric acid, lactic acid, malic acid) and derivatives thereof, sugars (e.g. inositol), alpha-hydroxy fatty acids, phytosterols, triterpene acids such as betulinic acid or ursolic acid, other macro- or microalgal extracts.

Advantageous osmolytes in this respect are quaternary amines, amino acids and polyols. Preferred osmolytes are, furthermore: substances from the group of sugar alcohols (myo-inositol, mannitol, sorbitol), taurin, choline, betaine, betaine glycine, ectoine, diglycerol phosphate, phosphorylcholine, glycerophosphorylcholines, glutamine, glycine, alanine, glutamate, aspartate or proline, phosphatidylcholine, phosphatidylinositol, inorganic phosphates, proteins, peptides, polyamine acids and polyols.

Products according to the present invention may comprise one or more compatible solutes. Preferred compatible solutes are described in WO 01/76572, namely dimyo-inositol phosphate (DIP), diglycerin phospate (DGP), di-myo-inositol phosphate (DIP), cyclic 2,3 diphosphoglycerate (cDPG), 1,1-di-glycerol phosphate (DGP), beta-mannosyl glycerate (firoin), beta-mannosyl glyceramide (firoin-A) and di-mannosyl-di-inositol phosphate (DMIP) and ectoine and ectoine-derivatives, as described in EP 0 553 884 A, EP 0 671 161 A and WO 94/15923, in particular ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidinecarboxylic acid).

Preferably, the total amount of compatible solutes is in the range of from 0.05 to 10 wt.-%, preferably 0.1 to 5 wt.-%, based on the total weight of the product according to the present invention.

Also preferred are products according to the present invention comprising one or more cooling agents selected from the group consisting of: menthol, preferably l-menthol, menthone glycerin acetal (trade name: Frescolat® MGA), menthyl lactate (preferably 1-menthyl lactate, in particular 1-menthyl-l-lactate, trade name: Frescolat® ML), substituted menthyl-3-carboxylic acid amide (e.g. menthyl-3-carboxylic acid-N-ethylamide), 2-isopropyl-N-2,3-trimethylbutanamide, substituted cyclohexane carboxylic acid amide, 3-menthoxypropane-1,2-diol, 2-hydroxyethylmenthylcarbonate, 2-hydroxypropylmenthylcarbonate, N-acetyl glycine menthyl ester, Isopulegol, menthyl hydroxycarboxylic acid ester (e.g. menthyl-3-hydroxybutyrate), monomenthylsuccinate, 2-mercaptocyclodecanone, menthyl-2-pyrrolidin-5-one carboxylate, 2,3-dihydroxy-p-menthane, 3,3,5-trimethyl cyclohexanone glycerine ketal, 3-menthyl-3,6-di- and -trioxa Ikanoate, 3-menthylmethoxy acetate, N-(4-cyanomethylphenyl)-p-menthanecarboxamide, N-(4-cyanophenyl)-p-menthanecarboxamide and Icilin.

Preferred cooling agents are: l-menthol, menthone glycerine acetal (trade name: Frescolat® MGA), menthyl lactate (preferably 1-menthyl lactate, in particular l-menthyl-l-lactate, trade name: Frescolat® ML), 3-menthoxy propane-1, 2-diol, 2-hydroxyethyl menthyl carbonate, 2-hydroxypropyl menthyl carbonate, particular preference being for l-menthyl-l-lactate.

Products according to the present invention may comprise one or more anti-cellulite agents as well as agents enhancing or boosting the activity of anti-cellulite agents.

Anti-cellulite agents and lipolytic agents are preferably selected from the group consisting of those described in WO 2007/077541, and beta-adrenergic receptor agonists such as synephrine and its derivatives.

Agents enhancing or boosting the activity of anti-cellulite agents, in particular agents which stimulate and/or depolarise C nerve fibres, are preferably selected from the group consisting of capsaicin and derivatives thereof, vanillyl-nonylamid and derivatives thereof, L-carnitine, coenzym A, isoflavonoides, soy extracts, *ananas* extract and conjugated linoleic acid.

For certain products according to the present invention are preferred which in addition comprise one, two or more compounds of the group consisting of:
glycerol, 1,2-propanediol, 1,3-propanediol, 1,2-butanediol, 1,3-butanediol, 1,4-butanediol, 2,3-butanediol, 1,2-pentanediol, 1,5-pentanediol, 1,2-hexanediol, 1,6-hexanediol, 1,2-octanediol, 1,8-octanediol, 2-methylpentane-2,4-diol, 2,5-hexanediol, 3,6-octanediol, 2-ethyl-1,3-hexanediol, 1,3-octanediol, 1,2-decanediol, 1,3-decanediol, 1,2-dodecandiol, 1,2-tetradecandiol.

Products of the present invention in addition may additionally comprise known antimicrobials like chitosan, totarol, farnesol, glycerol monolaurate, arylalkyl alcohols, such as e.g. 4-methyl-4-phenyl-2-pentanol and its derivatives (DE 101 43 434 A1, in particular 4-methyl-4-phenyl-2-pentanol), muguet alcohol (2,2-dimethyl-3-phenylpropanol), other arylalkyl alcohols (e.g. as disclosed in DE 44 47 361 A1, DE 103 30 697 A1, U.S. Pat. No. 4,110,430 or EP 1 157 687 A2), 2-butyloctanoic acid, 2-hexyldecanoic acid, p-anisic acid, essential oils with antimicrobial properties and isolates from essential oils with antimicrobial properties like e.g. thymol or eugenol, perfume oils or single aroma chemicals with antimicrobial activity, polyglycerol esters, such as e.g. polyglyceryl 3-caprylates, or combinations of the substances mentioned, which are generally employed, inter alia, against underarm odor, foot odor, acne or dandruff formation.

In products of the present invention a combination with (metal) chelators is advantageous in some cases. (Metal) chelators which are preferably to be employed here are, inter alia, α-hydroxy fatty acids, phytic acid, lactoferrin, α-hydroxy acids, such as, inter alia, citric acid, lactic acid and malic acid, and humic acids, bile acids, bile extracts, bilirubin, biliverdin or EDTA, EGTA and derivatives thereof.

The invention is further described by the following figures and examples, without limiting the scope of the claims. Unless indicated otherwise, all data, in particular ratios and percentages, refer to the weight.

Abbreviations used:
EPA=eicosapentaenoic acid (C20:5); PUFAs=polyunsaturated fatty acids; W:V=weight:volume.

The strain "OR" of *Tetraselmis suecica* used in the following experiments was obtained from the University of Florence.

EXTRACTION EXAMPLE 1

Preparation of "Direct Extracts"

*Tetraselmis suecica* (Tetra) was used to prepare extracts by the following steps:
1. Prepare a suspension of powdery freeze-dried *Tetraselmis* cell material in the selected extractant at a ratio (dry weight/volume) of 10 mg:1 ml;
2. stir the suspension in the dark at room temperature (18-23° C.) for 16 h;
3. centrifuge the suspension at 2000 g for 15 minutes to recover a supernatant and a cell material pellet;
4. resuspend the pellet in 0.5 ml of the aforementioned selected extractant for each ml used at the step 1;
5. immediately centrifuge the suspension at 2000 g for 15 minutes to recover a supernatant and a cell material pellet;
6. repeat steps 4 and 5 one more time;
7. combine the supernatants to form the "direct extract" of the respective extractant.

The extractant was chosen from water, methanol, ethanol, isopropanol, ethyl acetate and hexane:

TABLE 1

Ratio of dry extract/biomass (dry weight) with different extractants

| Extractant | % of the dried biomass |
|---|---|
| Water | 32 |
| Methanol (MeOH) | 17 |
| Ethanol (EtOH) | 15 |
| Iso-propanol (Isop-OH) | 3 |
| Ethylacetate (EtAc) | 7 |
| Hexane | 5 |

EXTRACTION EXAMPLE 2

Preparation of "Sequential Extracts"

For preparation of "sequential extracts", first a direct extract was prepared. After step 6, the cell material pellet was resuspended in a selected further extractant, and steps 3 to 7 were then performed again with the selected further extractants.

A series of sequential extractions was produced according to table 2:

TABLE 2 sequential extracts and related ratio of extract/biomass in dry weight

| Sequential protocol | Extractant | Extract symbol | % ratio dry extract/biomass |
|---|---|---|---|
| Ethyl acetate followed by 30% ethanol | Ethyl acetate 30% Ethanol | dir-EtAc seq. 30% EtOH | 5 |
| Methanol followed by water | Methanol Water | dir MeOH seq water2 | 17 |
| Hexane followed by ethyl acetate | Hexane Ethyl acetate | dir-Hex seq-EtAc | 5 3 |
| followed by ethanol followed by water | Ethanol Water | seq-EtOH seq-Water | 10 25 |

EFFECTS EXAMPLES

The content of polyunsaturated fatty acids (PUFAs) [eicosapentaenoic acid (EPA) (020:5), 020:4 (calculated as C18:4), stearidonic acid (C18:4), linolenic (C18:3), linolic acid (C18:2), C16:4 (calculated as C18:4) and C16:3 (calculated as 018:3)] in the respective extracts was determined.

Modulation of Hair Follicle Growth

Examples 1 and 2

Activity of Methanol Extract (Dir-MeOH) from *Tetraselmis* on the Metabolism of Hair Follicles The following experiment was conducted to demonstrate the activity of the direct methanol extract (dir-MeOH) on hair follicle growth.

All the experimental groups and the control were prepared comprising 12-18 follicles, plated at the density of 3 hair follicles/well in 24 well plates. Hair follicles were taken from the scalp of six donors and transferred for cultivation in sterile 24 well plates using a modified Williams' Medium E. Cultivation took place for nine days, following 18 h of pre-incubation performed in order to select hair follicles suitable to be maintained in culture. Only those follicles showing a good vital stage and a growth of not less than 0.2 mm have been used for the experiments.

The growth performances observed in the treated hair follicles have been compared to a control group, which was cultured in the same culture medium but free from extract supplement.

The experimental design consisted in treatments with dir-MeOH extract at two final concentrations corresponding to 0.1 and 10 μg/ml. In order to obtain these supplemented media, the required quantity of MeOH extract was submitted to solvent evaporation and then solved again in DMSO. The final concentration of this DMSO-solved extract has been modulated in order to supplement the experimental media with the desired extract quantity, obtaining at same time a final concentration in DMSO equal to 0.05%. The same concentration of DMSO has been also reached in the medium for the culture of the control group.

The activity of the microalgae treatment is demonstrated by the reduction of hair follicle growth expressed as percentage variation in comparison to the elongation performed by the control group. The experiments were terminated after 9 days of cultivation (8 of treatment). The growth of the hair follicles was studied by microphotography and subsequently determined by image analysis. All the hair follicles were photographed every two days.

The results have been compiled in Table 3, where the hair follicle elongation is expressed as percentage ratio between the experimental groups and the untreated control.

TABLE 3

Growth of hair follicles at day 9 of culture - Data pooled from six donors
Elongation in [%] of the control performance ± standard error

| Ex. | Experimental treatment | Growth (%) | Standard error | N. of Hair follicles | ANOVA Test | EPA medium content | PUFAs medium content |
|---|---|---|---|---|---|---|---|
| 0 | Control | 100.0 | 2.0 | 80.0 | — | — | — |
| 1 | dir-MeOH extract 0.1 μg/ml | 91.8 | 2.4 | 57 | P < 0.01 | 0.00001 | 0.00192 |
| 2 | dir-MeOH extract 10 μg/ml | 90.0 | 2.3 | 55 | p < 0.01 | 0.001 | 0.192 |

The results indicate that the addition of MeOH extract leads to a significant decrease in growth of the hair follicles in comparison to the untreated group.

Examples 3 and 4

Activity of Methanol Extract (Dir-MeOH) from *Tetraselmis* on the Metabolism of Hair Follicles The same experimental protocol described for the examples 1 and 2 has been repeated to investigate the activity of dir-MeOH extract at lower concentration. Two experimental replicates were performed treating hair follicles, taken from two different donors, at extract concentrations 0.01 μg/ml and 1 μg/ml.

The following data have been obtained.

TABLE 4

Growth of hair follicles at day 9 of culture - Data pooled from two replicates
Elongation in [%] of the control performance ± standard error

| Ex. | Experimental Treatment | Growth (%) | Standard error | N. of Hair follicles | ANOVA Test | EPA medium content | PUFAs medium content |
|---|---|---|---|---|---|---|---|
| 0 | Control | 100.0 | 2.8 | 32 | — | — | — |
| 3 | dir-MeOH extract 0.01 μg/ml | 89.0 | 4.1 | 23 | P < 0.05 | 0.000001 | 0.000192 |
| 4 | dir-MeOH extract 1 μg/ml | 89.5 | 3.4 | 23 | P < 0.05 | 0.0001 | 0.0192 |

The presented data confirm that the dir-MeOH extract modulates of the hair follicle growth producing a reduction of growth significant on statistical basis (P<0.05).

Example 5
Activity of Isopropanol Extract (Dir-Isopropanol) from *Tetraselmis* on the Metabolism of Hair Follicles The same experimental protocol described for the examples 1 and 2 has been repeated to investigate the activity of the dir-Isopropanol extract. The hair follicles taken from a single donor have been treated supplementing the experimental media with the extract at a concentration of 0.1 µg/ml. The following data were obtained.

TABLE 5

Growth of hair follicles at day 9 of culture - Data from a single donor
Elongation in [%] of the control performance ± standard error

| Ex. | Experimental Treatment | Growth (%) | Standard error | N. of Hair follicles | ANOVA Test | EPA medium content | PUFAs medium content |
|---|---|---|---|---|---|---|---|
| 0 | Control | 100.0 | 4.3 | 18 | — | — | — |
| 5 | dir-Isopropanol extract 0.1 µg/ml | 89.2 | 5.6 | 12 | n.s. | 0.00001 | 0.00079 |

Example 6
Activity of Isopropanol Extract (Dir-Isopropanol) from *Tetraselmis* on the Metabolism of Hair Follicles The previous experiment was repeated by using hair follicle taken from a different donor, in order to confirm the inhibiting action of the dir-Isopropanol extract. The following data were obtained.

TABLE 6

Growth of hair follicles at day 9 of culture - Data from a single donor
Elongation in [%] of the control performance ± standard error

| Ex. | Experimental Treatment | Growth (%) | Standard error | N. of Hair follicles | ANOVA Test | EPA medium content | PUFAs medium content |
|---|---|---|---|---|---|---|---|
| 0 | Control | 100.0 | 3.6 | 18 | — | — | — |
| 6 | dir-Isopropanol extract 1 µg/ml | 86.4 | 6.6 | 11 | P < 0.05 | 0.0001 | 0.0079 |

As in the previous experiment, a significant reduction in growth has been recorded (about −14%). This occurred treating the follicles at 1 µg/ml, suggesting that this donor was less sensitive to the inhibiting active in comparison to the previous one. In this case, however, the growth inhibition resulted significant also on statistical basis (P<0.05).

Examples 7 to 9
Activity of Ethanol Extract (Dir-EtOH) from *Tetraselmis* on the Metabolism of Hair Follicles The same experimental protocol described for the examples 1 and 2 has been repeated to investigate the activity of the dir-Ethanol extract. The hair follicles taken from a single donor have been treated supplementing the experimental media with the extract at concentrations at 0.01 µg/ml, 1 µg/ml and 10 µg/ml. The following data were obtained.

TABLE 6

Growth of hair follicles at day 9 of culture - Data from a single donor
Elongation in [%] of the control performance ± standard error

| Ex. | Experimental Treatment | Growth (%) | Standard error | N. of Hair follicles | ANOVA Test | EPA medium content | PUFAs medium content |
|---|---|---|---|---|---|---|---|
| 0 | Control | 100.0 | 3.2 | 15 | — | — | — |
| 7 | dir-Ethanol extract 0.01 µg/ml | 84.0 | 6.1 | 10 | P < 0.05 | 0.000010 | 0.000244 |
| 8 | dir-Ethanol extract 1 µg/ml | 86.7 | 3.2 | 9 | P < 0.05 | 0.0010 | 0.0244 |
| 9 | dir-Ethanol extract 10 µg/ml | 89.8 | 5.9 | 9 | n.s. | 0.010 | 0.244 |

A general inhibition of hair follicle growth has been obtained as response to the treatments. The most relevant reduction of growth (−16%) has been observed by treating hair follicle with dir-EtOH extract at 0.01 µg/ml.

Examples 10 to 17

Activity of Four-Steps Sequential Extracts (Dir-Hex>Seq-EtAc>Seq-EtOH>Seq-Water) from *Tetraselmis* on the Metabolism of Hair Follicles The same experimental protocol described for the examples 1 and 2 has been repeated to investigate the activity of sequential extracts prepared following the "four-steps sequential extraction" yet described.

Four extracts have been prepared (dir-HEX>seq-EtAc>seq-EtOH>seq-Water) and three dose treatments have been tested for each of them, using hair follicles obtained from a single donor. The experiment has been replicated twice and the data have been pooled to represent the average response of the two donors:

The experiments attest that two or three classes of compounds active on hair growth have been separated in the sequential extracts: the first has been mainly extracted by hexane and it produced a significant decrease (P<0.01) of hair growth at 10 µg/ml. The EtAc also resulted an effective extracting solvent with regard to a lipophilic active compound, that probably is the same residual from previous extraction performed by hexane. However, also the seq-EtAc produced a significant inhibition of hair follicle growth at 0.1 µg/ml (P<0.05).

A second compound resulted concentrated in the seq-ethanol extract, which gave the most intense response by treating at 1 µg/ml (P<0.01). The seq-water extract also produced a very significant inhibition of the HF growth. The best response has been obtained by treating at 1 µg/ml (P<0.01)

Modulation of Pigmentation

Experiments designed in order to highlight activity on pigmentation, have been performed using both two-steps

TABLE 7

Growth of hair follicles at day 9 of culture - Data pooled from two replicates
Elongation in [%] of the control performance ± standard error

| Ex. | Experimental treatment | Growth (%) | Standard error | N. of Hair follicles | ANOVA Test | EPA medium content | PUFAs medium content |
|---|---|---|---|---|---|---|---|
| 0 | Control | 100.0 | 3.0 | 24 | — | — | — |
| 10 | Dir-Hex extract 0.1 µg/ml | 99.0 | 4.5 | 21 | n.s. | 0.0000004 | 0.000189 |
| 11 | Dir-Hex extract 1 µg/ml | 90.1 | 2.3 | 22 | P < 0.05 | 0.000004 | 0.00189 |
| 12 | Dir-Hex extract 10 µg/ml | 81.4 | 3.7 | 22 | P < 0.01 | 0.00004 | 0.0189 |
| 13 | Seq-EtAc extract 0.1 µg/ml | 88.7 | 3.1 | 22 | P < 0.05 | 0.0000010 | 0.000252 |
| 14 | Seq-EtOH extract 0.1 µg/ml | 90.1 | 4.0 | 24 | P < 0.05 | 0.0000010 | 0.00050 |
| 15 | Seq-EtOH extract 1 µg/ml | 85.8 | 2.8 | 22 | P < 0.01 | 0.000010 | 0.0050 |
| 16 | Seq-Water extract 0.1 µg/ml | 96.2 | 2.7 | 22 | n.s. | 0 | 0.000025 |
| 17 | Seq-Water extract 1 µg/ml | 86.7 | 3.1 | 22 | P < 0.01 | 0 | 0.00025 |

(dir-EtAc>seq-30% EtOH) and four-steps sequential extracts (dir-Hex>seq-EtAc>seq-EtOH>seq-Water), prepared as described above.

The modulation of melanin synthesis has been tested on both hair follicles and skin.

The experiments had the aim to verify if more actives are present in the Tetra biomass and if they could be separated throughout sequential extractions.

Examples 18 to 21

Activity of Dir-EtAc and Seq-30% EtOH Extracts (Two-Steps Sequential Extracts) on Hair Follicles Pigmentation The hair follicle culture technique was the same described for the examples 1 and 2, but the culture was stopped at day 5 for performing the melanin content analysis. In order to detect the melanin content in hair follicle's dermopapillas, histological slides have been set up and then stained according to the Fontana-Masson technique. The dermopapilla's melanin content have been detected by computerised image analysis.

The activity on pigmentation of both lipophilic (dir-EtAc) and hydrophilic (seq-30% EtOH) extracts has been studied by performing an experiment with a biological sample taken from a single donor. The culture media for the experimental treatments were prepared according to the previous descriptions.

The hair follicles culture was terminated after 5 days of cultivation (4 of treatment). The melanin content of the tissues surrounding dermopapillas was detected by image analysis and the results are shown in Table 8.

TABLE 8

Melanin content of hair follicles at day 5 of culture - Data from single donor
Melanin content in [%] of the control performance ± standard error

| Ex. | Experimental Treatment | Melanin content (%) | Standard error | N. of Samples | ANOVA Test |
|---|---|---|---|---|---|
| 0 | Control | 0.0 | 11.4 | 12 | |
| 18 | dir-EtAc 0.1 µg/ml | −25.2 | 6.3 | 12 | n.s. |
| 19 | dir-EtAc 1 µg/ml | −20.9 | 9.7 | 12 | n.s. |
| 20 | Seq-30% EtOH 1 µg/ml | −9.4 | 9.6 | 12 | n.s. |
| 21 | Seq-30% EtOH 10 µg/ml | −25.6 | 9.8 | 12 | n.s. |

The results clearly indicate that the treatment of hair follicles with the microalgae extracts decreased the content of melanin after 4 days of treatment. The intensity of the response varied with the dose-treatment. However, the more intensive responses have been detected by treating with dir-EtAc extract at 0.1 µg/ml and with seq-30% EtOH extract at 10 µg/ml.

Examples 22 to 24

Activity of Ethanol Extract (Dir-EtOH) on Skin Pigmentation

In order to better explore the biological modulation properties of the extracts obtained from *Tetraselmis*, some experiments have been performed testing their effects on skin pigmentation.

Organ culture of full thickness human skin has been performed starting from a skin sample, exciding pieces of about 4×4 mm and culturing them up to day six. The culture medium was a modified William-E and it has been changed at day three.

The present experiment was designed in order to detect active compounds in extracts obtained by using direct ethanol and, at the same time, to verify if these compounds were detectable in biomasses of the same algal strain, harvested from replicated cultures. Two dir-EtOH extracts were prepared from different biomasses of the same strain of *Tetraselmis*, labelled as Tetra1 and Tetra2. The extracts were air-dried and then solved in a quantity of DMSO suitable to obtain a final concentration of 1 and 10 µg/ml. The experimental treatments were daily performed by topical application of 5 µl of extract on the cultured skin samples.

After six days of organ culture, histological section were prepared from the skin samples and the quantitative changes of melanin content have been investigated following Fontana-Masson staining technique. The melanin quantification was obtained by image analysis of microphotographs of each histological skin section. The results are shown in Table 9.

TABLE 9

Melanin content of skin samples at day 6 of culture - Data from single donor
Melanin content in [%] of the control performance ± standard error

| Ex. | Experimental Treatment | Melanin content (%) | Standard error | N. of Samples | ANOVA Test |
|---|---|---|---|---|---|
| 0 | Control | 100 | 10.8 | 8 | |
| 22 | Tetra1 dir-EtOH 1 µg/ml | 72.0 | 6.5 | 8 | n.s. |
| 23 | Tetra1 dir-EtOH 10 µg/ml | 79.5 | 12.6 | 8 | $P < 0.05$ |
| 24 | Tetra2 dir-EtOH 10 µg/ml | 74.0 | 7.9 | 8 | n.s. |

The extracts obtained from both the biomasses produced a relevant inhibition of the melanin content in the skin samples of up to 28% in comparison to the control group. The most intense response has been obtained by treating skin with 1 µg/ml of the dir-EtOH extract related to the biomass Tetra1 ($P < 0.05$).

Examples 25 to 32

Activity of Four-Steps Sequential Extracts (Dir-Hex>Seq-EtAc>Seq-EtOH>Seq-Water) from *Tetraselmis* on Skin Pigmentation The same protocol of the previous experiment has been adopted to test activity on the skin pigmentation related with the four-steps extracts (dir-Hex>seq-EtAc>seq-EtOH>seq-Water) prepared from *Tetraselmis* biomass as described at the beginning of the document.

In this experiment, differently from the previous protocol, treatments at the concentrations of 5 and 50 µg/ml were performed for each extract. The results are reported in Table 10

TABLE 10

Melanin content of skin samples at day 6 of culture - Data from single donor
Melanin content in [%] of the control performance ± standard error

| Ex. | Experimental treatment | Melanin content (%) | Standard error | N. of Samples | ANOVA Test | EPA medium content | PUFAs medium content |
|---|---|---|---|---|---|---|---|
| 0 | Control | 100.0 | 7.9 | 12 | — | — | — |
| 25 | Dir-Hex extract 5 µg/ml | 63.0 | 9.4 | 12 | P < 0.05 | 0.00002 | 0.0094 |
| 26 | Dir-Hex extract 50 µg/ml | 69.0 | 5.4 | 12 | P < 0.01 | 0.0002 | 0.094 |
| 27 | Seq-EtAc extract 5 µg/ml | 60.4 | 6.2 | 12 | P < 0.01 | 0.00005 | 0.0126 |
| 28 | Seq-EtAc extract 50 µg/ml | 60.6 | 9.5 | 12 | P < 0.01 | 0.0005 | 0.126 |
| 29 | Seq-EtOH extract 5 µg/ml | 56.7 | 9.1 | 12 | P < 0.01 | 0.00005 | 0.0250 |
| 30 | Seq-EtOH extract 50 µg/ml | 82.2 | 12.6 | 12 | n.s | 0.0005 | 0.250 |
| 31 | Seq-Water extract 5 µg/ml | 102.8 | 15.7 | 12 | n.s. | 0 | 0.0012 |
| 32 | Seq-Water extract 50 µg/ml | 117.3 | 7.9 | 12 | n.s. | 0 | 0.012 |

All the lipophilic extracts produced a very significant skin lightening (P<0.01). This activity was present also in the seq-EtOH (middle lipophilic), while disappear completely in the aqueous extract, which weakly stimulated pigmentation. Regularly Activity on the Epidermal Cornified Cell Envelope On the skin, the cornified envelope (CE) is obtained by progressive sclerification of the keratinocyte to corneocyte. This process implies the progressive synthesis and storage of specific proteins which can be modulated in order to vary the CE thickness.

It has been shown that a moderate increase in thickness of the CE induces a better skin moisturizing.

The present experiment has been designed in order to investigate possible activities of the sequential extracts obtained from *Tetraselmis*, with regard to modulation of the synthetic metabolism of involucrin and filaggrin, two essential components of the epidermal CE.

Examples 33 to 40

Activity of Four-Steps Sequential Extracts (Dir-Hex>Seq-EtAc>Seq-EtOH>Seq-Water) from *Tetraselmis* on the Involucrin Synthesis Performed by Skin Keratinocytes Skin samples has been cultured and treated as described for the examples 25 to 32. The sequential extracts have been prepared as described at the beginning of this document. At day 6 of culture, the skin samples were embedded in an appropriate medium (Cryomatrix, Thermo Shandon Ltd.) and frozen in liquid nitrogen.

In order to perform the quantitative analysis of the involucrin, some cryostat sections have been prepared and submitted to specific immunofluorescence staining.

Histological sections of each sample have been analysed for their involucrin content. Each slide has been photographed by using a fluorescence microscope and the resulting image analysed in order to obtain a quantitative estimation of the fluorescent signal. This analysis was performed by using a customised software tool. The protein quantification of the samples treated with sequential extracts is shown in Table 11

TABLE 11

Involucrin content in skin epidermal tissue at day 6 of culture - Data pooled from single donor
Protein quantification in [%] by comparison to control ± standard error

| Ex. | Experimental Treatment | Involucrin content (%) | Standard error | N. of Samples | ANOVA Test |
|---|---|---|---|---|---|
| 0 | Control | 100.0 | 17.7 | 6 | |
| 33 | Dir-Hex extract 5 µg/ml | 132.7 | 9.5 | 6 | n.s |
| 34 | Dir-Hex extract 50 µg/ml | 158.3 | 11.1 | 6 | P < 0.01 |
| 35 | Seq-EtAc extract 5 µg/ml | 154.7 | 14.8 | 6 | P < 0.05 |
| 36 | Seq-EtAc extract 50 µg/ml | 180.5 | 22.9 | 6 | P < 0.01 |
| 37 | Seq-EtOH extract 5 µg/ml | 163.4 | 15.3 | 6 | P < 0.01 |
| 38 | Seq-EtOH extract 50 µg/ml | 150.2 | 18.3 | 6 | P < 0.05 |
| 39 | Seq-Water extract 5 µg/ml | 143.4 | 7.8 | 6 | P < 0.05 |
| 40 | Seq-Water extract 50 µg/ml | 178.6 | 7.7 | 6 | P < 0.01 |

The results attest that all the extracts induced a significant, or very significant, stimulation of involucrin synthesis. This allows to exploit the extracts for skin treatment in order to obtain a modulation of the epidermal cornified envelope.

The most effective extracts resulted to be the seq-EtAc and the seq-Water at the higher concentrations.

Examples 41 to 48

Activity of Four-Steps Sequential Extracts (Dir-Hex>Seq-EtAc>Seq-EtOH>Seq-Water) from *Tetraselmis* on the Filaggrin Synthesis Performed by Skin Keratynocites The protocol followed for the previous experiment has been repeated in order to investigate the activity of the sequential extracts on epidermal synthesis of filaggrin, another basic component of the CE. The aim was to verify if the involucrin stimulation was representative of a general stimulant action on the protein components of the cornified envelope. The results are shown in Table 12.

TABLE 12

Filaggrin content in skin epidermal tissue at day 6 of culture - Data pooled from single donor
Protein quantification in [%] by comparison to control ± standard error

| Ex. | Experimental Treatment | Filaggrin Content (%) | Standard error | N. of Samples | ANOVA Test |
|---|---|---|---|---|---|
| 0 | Control | 100.0 | 3.8 | 6 | |
| 41 | Dir-Hex extract 5 µg/ml | 92.4 | 8.2 | 6 | n.s. |
| 42 | Dir-Hex extract 50 µg/ml | 120.4 | 17.9 | 6 | n.s. |
| 43 | Seq-EtAc extract 5 µg/ml | 185.8 | 37.9 | 6 | P < 0.05 |
| 44 | Seq-EtAc extract 50 µg/ml | 186.6 | 22.1 | 6 | P < 0.05 |
| 45 | Seq-EtOH extract 5 µg/ml | 347.7 | 44.3 | 6 | P < 0.01 |
| 46 | Seq-EtOH extract 50 µg/ml | 180.1 | 28.0 | 6 | n.s. |
| 47 | Seq-Water extract 5 µg/ml | 279.3 | 31.7 | 6 | P < 0.01 |
| 48 | Seq-Water extract 50 µg/ml | 262.3 | 33.6 | 6 | P < 0.01 |

The results are very consistent with data related to involucrin synthesis. A general stimulant activity has been observed, while only the hexane extract did not produced the expected effects. Seq-EtOH and seq-Water resulted to perform the most intense stimulation of the filaggrin synthesis.

Modulation of Hair Follicle Growth

Examples 49 and 50

Activity of Ethyl Acetate Extract (Dir-EtAc) from *Tetraselmis* on the Metabolism of Hair Follicles The same experimental protocol described for the examples 1 and 2 has been repeated to investigate the activity of the dir-ethyl acetate extract. Three experimental replicates were performed treating hair follicles, taken from three different donors, at extract concentrations 1 µg/ml and 10 µg/ml.

TABLE 13

Growth of hair follicles at day 9 of culture - Data from three donors
Elongation in [%] of the control performance ± standard error

| Ex. | Experimental Treatment | Growth (%) | Standard error | N. of Hair follicles | ANOVA Test |
|---|---|---|---|---|---|
| 0 | Control | 100.0 | 2.5 | 41 | |
| 49 | dir-EtAc extract 1 µg/ml | 91.7 | 2.8 | 31 | P < 0.05 |
| 50 | dir-EtAc extract 10 µg/ml | 94.5 | 2.8 | 28 | n.s. |

The presented data confirm that the dir-EtAc extract reduces the hair follicle growth significantly on statistical basis ($P<0.05$).

Modulation of Pigmentation

Examples 51 and 52

Activity of Methanol Extract (Dir-MeOH) from *Tetraselmis* on Skin Pigmentation

The same experimental protocol described for the examples 22 to 24 has been repeated to investigate the modulatory activity of the methanol extract on skin pigmentation. Skin samples obtained from two different donors have been tested in two subsequent experiments.

TABLE 14

Melanin content of skin samples at day 6 of culture - Data from two donors
Melanin content in [%] of the control performance ± standard error

| Ex. | Experimental Treatment | Melanin content (%) | Standard error | N. of Samples | ANOVA Test |
|---|---|---|---|---|---|
| 0 | Control | 100 | 6.3 | 20 | |
| 51 | dir-MeOH 1 µg/ml | 89.0 | 5.9 | 16 | n.s. |
| 52 | dir-MeOH 10 µg/ml | 81.5 | 6.8 | 16 | P < 0.05 |

The results clearly show that the treatment of the skin samples with the methanol extract decreased the content of melanin after 6 days of treatment. A significant melanin reduction of 18.5% in comparison to the control group was obtained by treatment with methanol extract at a concentration of 10 µg/ml.

Examples 53 to 58

Activity of Ethyl Acetate Extract (Dir-EtAc) from *Tetraselmis* on Skin Pigmentation The same experimental protocol described for the examples 22 to 24 has been adopted to test the activity of the ethyl acetate extract and at the same time to compare the activity of extracts obtained from four different biomass batches of the same *Tetraselmis* strain (i.e. harvested at different time points of culture), labelled as Tetra1 to Tetra3. Skin samples obtained from three different donors have been tested in three subsequent experiments.

TABLE 15

Melanin content of skin samples at day 6 of culture - Data from three donor
Melanin content in [%] of the control performance ± standard error

| Ex. | Experimental Treatment | Melanin content (%) | Standard error | N. of Samples | ANOVA Test |
|---|---|---|---|---|---|
| 0 | Control | 100 | 3.3 | 36 | |
| 53 | Tetra1 dir-EtAc 1 µg/ml | 82.4 | 3.5 | 24 | $P < 0.001$ |
| 54 | Tetra1 dir-EtAc 10 µg/ml | 78.6 | 4.0 | 24 | $P < 0.001$ |
| 55 | Tetra2 dir-EtAc 1 µg/ml | 95.3 | 4.0 | 24 | n.s |
| 56 | Tetra2 dir-EtAc 10 µg/ml | 80.0 | 3.0 | 24 | $P < 0.001$ |
| 57 | Tetra3 dir-EtAc 1 µg/ml | 91.2 | 4.4 | 24 | n.s. |
| 58 | Tetra3 dir-EtAc 10 µg/ml | 74.7 | 5.5 | 24 | $P < 0.001$ |

The results clearly show that the treatment of skin samples with the ethyl acetate extracts decreased the content of melanin after 6 days of treatment. At a concentration of 10 µg/ml, a significant melanin reduction of 21.4, 20.0 and 25.3%, respectively, was observed for the three different biomass batches.

Product Examples 1-11

Skin Care

In Table 1 means
1=Moisturizing "water-in-oil" emulsion
2=Skin lightening "oil-in-water" emulsion with UVA/B broadband protection
3=Hair growth inhibiting and hair lightening "oil-in-water" cream
4=Skin tanning aerosol foam with UVB/UVA protection
5=Hair growth inhibiting post depilatory lotion O/W
6=Skin lightening and moisturizing balm
7=Skin lightening body spray O/W
8=Hair growth inhibiting shaving foam
9=Hair growth inhibiting after shave
10=Hair growth inhibiting and hair lightening antiperspirant pump spray
11=Hair growth inhibiting and hair lightening after shave hydro gel

TABLE 1

| RAW MATERIAL NAME (SUPPLIER) | INCI | 1 | 2 | 3 | 4 | 5 | 6 | 7 | 8 | 9 | 10 | 11 |
|---|---|---|---|---|---|---|---|---|---|---|---|---|
| | | | | | | | PPM | | | | | |
| Tetraselmis suecica dry extract | Tetraselmis Extract | 50 ppm | | | | | | | | | | |
| Tetraselmis suecica extract (dry extract content 1 wt %) | Maltodextrin, Tetraselmis Extract | | | | 500 ppm | | 10 ppm | | 25 ppm | | 100 ppm | |
| Tetraselmis suecica extract (dry extract content 0.5 wt %) | 1,2-Pentyleneglycol, Tetraselmis Extract | | | 100 ppm | | 400 ppm | | | | 600 ppm | | |
| Tetraselmis extract (dry extract content 0.2 wt %) | Glycerin, Water (Aqua), Pentylene Glycol, Tetraselmis Extract | | 500 ppm | | | | | 100 ppm | | | | 150 ppm |
| | | | | | | | WEIGHT % | | | | | |
| Abil 100 ® (Goldschmidt) | Dimethicone | 1.0 | | 2.0 | | | | | | | | |
| Alugel 34 TH (Baerlocher) | Aluminium Stearate | | | | | | | | | | | |
| Allantoin (Merck) | Allantoin | | | | | | | | | | | 0.1 |
| Aloe Vera Gel Concentrate 10/1 (Symrise) | Aloe Barbadensis Leaf Juice | | | | | | | | | | | 1.0 |
| alpha-Bisabolol (Symrise) | Bisabolol | 0.1 | | | 0.1 | | 0.2 | 0.1 | 0.05 | | | 0.05 |
| Beta-Arbutin | Arbutin | | | | | | 0.8 | 0.2 | | | | |
| Aristoflex AVC | Ammonium Acryloyldimethyltaurate/VP Copolymer | | | | | | | | 1.0 | | | |
| Avocado Oil (Symrise) | Persea Gratissima (Avocado) Oil | | | | | | | | | | | |
| Carbopol 2050 ® (B. F. Goodrich) | Carbomer | | | 0.1 | | | | | 0.1 | | | 0.4 |
| Carbopol Ultrez-10 (Noveon) | Carbomer | | 3.0 | | | | | | | | | |
| Corapan TQ ® (Symrise) | Diethylhexyl-1,6-Naphtalate | | | | | | | | 10.0 | | | |
| Cutina FS 45 (Cognis) | Stearic Acid, Palmitic Acid | | | | | | | | | | | |
| D-Panthenol (BASF) | Panthenol | | | | | | | 0.5 | | | | 0.5 |
| Dow Corning 345 Fluid | Cyvlomethicone | | | | | | | | | | | |
| Dragocid Liquid (Symrise) | Phenoxyethanol (and) Methylparaben (and) Ethylparaben (and) Butylparaben (and) Propylparaben (and) Isobutylparaben | 1.0 | 0.3 | 0.8 | 0.3 | 0.8 | | | 0.6 | | | |
| Dragosan W/O P (Symrise) | Sorbitan Isostearate, Hydrogenated Castor Oil, Ceresin, Beeswax (Cera Alba) | 7.0 | | | | | | | | | | |
| Dracorin CE | Glyceryl Stearate Citrate | | | | | 1.0 | | | | | | |
| Dracorin GMS (Symrise) | Glyceryl Stearate | | | | | 0.5 | | | | | | |
| Dracorin GOC (Symrise) | Glyceryl Oleate Citrate, Caprylic/Capric Triglyceride | | | 2.0 | 2.0 | | | 2.0 | | | | |
| Drago-Oat-Active | Water (Aqua), Butylene Glycol, Avina Sativa (Oat) Kernel Extract | | | | | | | 1.0 | | | | |
| Dragoxat 89 (Symrise) | Ethylhexyl Isononanoate | | | 3.0 | | 2.0 | 5.0 | 3.0 | | 1.0 | | |
| Dragoxat EH (Symrise) | Ethylhexyl Ethylhexanoate | | | | | | | | | | | |
| Edeta BD ® (BASF) | Dinatrium-EDTA | | 0.1 | 0.5 | 0.1 | | 0.1 | | | | | |
| Emulgade PL | Cetearyl Glucoside, Cetearyl Alcohol | | | 2.0 | | | | | | | | |
| Emulsiphos (Symrise) | Cetylphosphate, Hydrogenated Palm glycerides | | | | 1.5 | | | | | | | |
| Ethanol (96%) | Alcohol Denat. | | | | | | | | | 65.0 | | 8.0 |
| Extrapone Aloe Vera (Symrise) | Glyerin, Water (Aqua), Aloe Barbadensis Leaf Extract | 3.0 | | | | | | | | | | |

TABLE 1-continued

| RAW MATERIAL NAME (SUPPLIER) | INCI | 1 | 2 | 3 | 4 | 5 | 6 | 7 | 8 | 9 | 10 | 11 |
|---|---|---|---|---|---|---|---|---|---|---|---|---|
| Extrapone Chamomile (Symrise) | Glycerin, Water (Aqua), *Chamomilla Recutica* (*Matricaria*), Flower Extract | | | 0.5 | | | | | 1.0 | | | |
| Extrapone Green Tea (Symrise) | Glycerin, Water (Aqua), *Camallia Sinensis* Leaf Extract | | | 0.2 | | | | | | | | |
| Extrapone Rosemary (Symrise) | Glycerin, Water (Aqua), *Rosmarinus Officinalis* (Rosemary) Leaf Extract | | | 0.3 | | | | | | | | |
| Extrapone Witch Hazel (Symrise) | Propylene Glycol, *Hamamelis Virginiana* (Witch Hazel) Water, Water (Aqua), *Hamamelis Virginiana* (Witch Hazel) Extract | 1.0 | | | | | | | 1.0 | | | |
| Fragrance | Parfum (Fragrance) | 0.4 | 0.5 | 0.3 | 0.4 | 0.3 | 0.3 | 0.2 | 1.0 | 0.8 | 1.0 | 0.1 |
| Frescolat MGA (Symrise) | Menthone Glycerin Acetal | | | | | | | | 0.5 | | | |
| Frescolat ML (Symrise) | Menthyl Lactate | | | | | | | | | | | 0.3 |
| Glycerin 99% | Glycerin | 2.0 | 4.0 | 2.0 | 3.0 | 3.0 | | | 3.4 | | | |
| Hostacerin DGMS ® (Clariant) | Polyglyceryl-2-Stearate | | 3.0 | | | | 5.0 | 5.0 | | | 5.0 | 5.0 |
| Hydrolite-5 (Symrise) | 1,2-Pentyleneglycol | | | | | | | | | | | |
| Hydroviton 24 (Symrise) | Water (Aqua), Pentylene Gylcol, Glycerin, Sodium Lactate, Lactic Acid, Serine, Urea, Sorbitol, Sodium Chloride, Allantoin | 0.5 | | | | | | | | | | |
| Isoadipate (Symrise) | Diisopropyl Adipate | | | | | | | | | | | |
| Isodragol (Symrise) | Triisononanoin | | | 2.0 | | 2.0 | | | | 8.0 | | |
| Jojoba Oil (Symrise) | *Simmondsia Chinensis* (Jojoba) Seed Oil | | | | | | | | 1.0 | | | |
| Karion F (Merck) | Sorbitol | 2.0 | | | | | | | | | | |
| Keltrol T ® (Calgon) | Xanthan Gum | | 0.2 | 0.1 | | 0.2 | 0.2 | | | | | |
| Kojic acid | Kojic acid | | | | | | | | | | | |
| Lanette E ® (Cognis) | Natriumcetearylsulfat | | 0.7 | | | | | | | | | |
| Lanette O ® (Cognis) | Cetearyl Alcohol | | | 3.0 | | 1.0 | 5.0 | 5.0 | | | | |
| Lanette 16 ® (Cognis) | Cetyl alcohol | | 2.0 | | 0.5 | | | | | | | |
| Locron L (Cognis) | Aluminium Chlorohydrate | | | | | | | | | | | |
| Magnesium Sulfat Hepathydrat (Merck) | Magnesium Sulfate | 0.7 | | | | | | | | | | |
| Mineral Oil | Paraffinum Liquidum | | | | | | | 4.0 | | | | |
| NaOH 10% aq. solution | Sodium hydroxide | | 0.2 | | 2.9 | 0.45 | | 0.4 | | | | 0.75 |
| Neo Heliopan ® AP (Symrise), 15% as sodium salt | Dinatrium-Phenyldibenzimidazoltetrasulfonate | | 6.7 | | | | | | | | | |
| Neo Heliopan ® AV (Symrise) | Ethylhexylmethoxycinnamate | | | | 6.0 | | | | | | | |
| Neo Heliopan ® BB (Symrise) | Benzophenone-3 | | | | | | 0.25 | | | | | |
| Neo Heliopan ® 357 (Symrise) | Butyl Methoxydibenzoyl-methane | | 0.6 | | 1.5 | | | | | | | |
| Neo Heliopan ® HMS (Symrise) | Homosalate | | 9.5 | | | | | | | | | |
| Neo Heliopan ® Hydro (15% aq. solution neutralized with NaOH (Symrise) | Phenylbenzimidazol sulfonic acid | | 6.7 | | 13.3 | | | | | | | |
| Neo Heliopan ® MBC (Symrise) | 4-Methylbenzylidencampher | | | | 4.0 | | | | | | | |
| Neo-PCL Water Soluble N (Symrise) | Trideceth-9, PEG-5 Ethylhexanoate, Water (Aqua) | | | | | | | | | | 2.0 | 1.0 |
| Neutral oil (Symrise) | Caprylic/Capric Triglyceride | 12.0 | 5.0 | 0.25 | 2.0 | 2.0 | 3.0 | 4.0 | | | | |
| PCL liquid 100 (Symrise) | Cetearyl Ethylhexanoate | | | 5.0 | | 4.0 | 1.5 | 7.0 | | | | |
| PCL solid (Symrise) | Stearyl Heptanoate, Stearyl Caprylate | | | 2.0 | | | | | | | | |
| Pemulen TR-2 (Noveon) | Acrylates/C10-30 Alkyl Acrylate Crosspolymer | | | | | 0.15 | | 0.2 | | | | |
| Phenoxyethanol | Phenoxyethanol | | 0.7 | | 0.7 | | | | | | | |

TABLE 1-continued

| RAW MATERIAL NAME (SUPPLIER) | INCI | 1 | 2 | 3 | 4 | 5 | 6 | 7 | 8 | 9 | 10 | 11 |
|---|---|---|---|---|---|---|---|---|---|---|---|---|
| Plantacare 1200 UP (Cognis) | Lauryl Glucoside | | | | | | | | | | | |
| Prisorine 3505 ® (UniQema) | Isostearic acid | | 0.5 | | | | | | 4.0 | | | |
| 1,2-Propylenglycol 99% | Propylene Glycol | | | 5.0 | | 2.0 | | | | | 3.0 | 5.0 |
| SF1214 ® (Bayer) | Cyclopentasiloxane, Dimethicone | | 1.0 | | | | | | | | | |
| Sodium Benzoate | Sodium Benzoate | | | | | 0.1 | | | | | | |
| Solubilizer (Symrise) | PEG-40 Hydrogenated Castor Oil, Trideceth-9, Propylene Glycol, Water (Aqua) | | | | | | | | | | 3.0 | 1.3 |
| Sun Flower Oil (H. Erhard Wagner) | *Helianthus Annus* (Sunflower) Seed Oil | 5.0 | | | | | | | | | | |
| Sweet Almon Oil (H. Erhard Wagner) | *Prunus Dulcis* | 5.0 | | | | | | | | | | |
| SymCalmin (Symrise) | Butylene Glycol, Pentylene Glycol, Hydroxy-phenyl Propamidobenzoic Acid | | | | | 1.0 | | | | | | |
| SymDeo MPP (Symrise) | Dimethyl Phenyl 2-Butanol | | | | | | | | | | 0.5 | |
| Symdiol 68 (Symrise) | 1,2-Hexanediol, Caprylalcohol | | 0.5 | | | | | | | | | |
| SymGlucan (Symrise) | Water, Glycerin, Beta-Glucan | | | 0.3 | | | | | | | | |
| SymRelief (Symrise) | Bisabolol, *Zingiber Officinale* (Ginger) Root Extract | | | | | 0.2 | | | | 0.2 | | |
| SymWhite 377 (Symrise) | Phenylethyl Resorcinol | | | | | | 0.3 | | | | | |
| Tegosoft MM (Goldschmidt) | Myristyl Myristate | | 2.0 | | | 1.0 | | | | | | |
| Tegosoft TN ® (Goldschmidt) | C12-C15 Alkylbenzoate | | | | 2.0 | | | | | | | |
| Texapon N 70 (Cognis) | Sodium Laureth Sulfate | | | | 0.1 | | | | | | | |
| Triethanolamine 99% | Triethanolamine | | | | | | | | 5.0 | | | |
| Vitamin E Acetate (DSM Nutritional Products) | Tocopheryl Acetate | 3.0 | 0.5 | | 0.5 | | | | | | | |
| Vitamin A Palmitate in oil (1 Mio Ie/g) (DSM Nutritional Products) | Retinyl Palmitate | 0.2 | | | | | | | | | | |
| Water, demineralized | Aqua (Water) | ad 100 | ad 100 | ad 100 | ad 100 | ad 100 | ad 100 | ad 100 | ad 100 | ad 100 | ad 100 | ad 100 |

Product Examples 12-18

Hair Care

In Table 2 means
12=Hair growth inhibiting hair tonic
13=Hair tanning 2 in 1 after sun shampoo
14=Hair lightening conditioner with UVB/UVA protection
15=Hair growth inhibiting liquid hair leave-on, pump-foam for dyed hair
16=Hair growth inhibiting styling gel
17=Anti-dandruff shampoo
18=Colour toning shampoo blonde

TABLE 2

| RAW MATERIAL NAME (SUPPLIER) | INCI | 12 | 13 | 14 | 15 | 16 | 17 | 18 |
|---|---|---|---|---|---|---|---|---|
| | | | | PPM | | | | |
| *Tetraselmis suecica* dry extract | *Tetraselmis* Extract | | | 50 ppm | | | | 10 ppm |
| *Tetraselmis* extract (dry extract content 0.5 wt %) | Maltodextrin, *Tetraselmis* Extract | 100 ppm | | | | | | |
| *Tetraselmis* extract (dry extract content 0.25 wt %) | 1,2-Pentyleneglycol, Water, *Tetraselmis* Extract | | | | 400 ppm | 40 ppm | | |
| *Tetraselmis* extract (dry extract content 2 wt %) | Propylene Glycol, Water (Aqua), PEG-40 Hydrogenated Castor Oil, Trideceth-9, *Tetraselmis* Extract | | | | 500 ppm | | 150 ppm | |
| | | | | WEIGHT % | | | | |
| Abil B 9950 (Evonic Goldschmidt) | Dimethicone Propyl Pg-Betaine | | | | 0.2 | | | |
| Abil-Quat 3272 (Evonic Goldschmidt) | Quaternium-80 | | | | 0.5 | | | |
| Actipone Alpha Pulp (Symrise) | Water (Aqua), Butylene Glycol, Malic Acid, *Actinidia Chinensis* (Kiwi) Fruit Juice, Citrus *Aurantium Dulcis* (Orange) Juice, Citrus *Paradisi* (Grapefruit) Juice, *Pyrus Malus* (Apple) Juice, Trideceth-9, *Prunus Amygdalus Dulcis* (Sweet Almond) Seed Extract | | | | 0.75 | | | |
| *Aloe Vera* Gel Concentrate 10/1 (Symrise) | Water (Aqua), *Aloe Barbadensis* Leaf Juice | | 0.5 | | | | | |
| -(-Alpha-)-Bisabolol, natural (Symrise) | Bisabolol | | | | | | 0.1 | |
| Antil 141 Liquid (Evonic Goldschmidt) | Propylene Glycol, PEG-55 Propylene Glycol Distearate | | 1.0 | | | | | |
| Antil 171 (Evonic Goldschmidt) | PEG-18 Glyceryl Oleate/Cocoate | | | | | | 2.0 | |
| Antil 200 (Evonic Goldschmidt) | PEG-200-Hydrogenated Glyceryl Palmate, PEG-7 Glyceryl Cocoate | | | | | | | 1.5 |
| Brilliant Blue No. 1 1% solution in water (Symrise) | Blue 1, C.I. 42090 | 0.02 | | | | | | |
| Carbopol ETD 2001 (Noveon) | Carbomer | | | | | 0.7 | | |

TABLE 2-continued

| RAW MATERIAL NAME (SUPPLIER) | INCI | 12 | 13 | 14 | 15 | 16 | 17 | 18 |
|---|---|---|---|---|---|---|---|---|
| Celquat L-200 (National Starch & Chemical) | Polyquaternium-4 | | | | 1.0 | | | |
| CeramideBio | N-(1-Hexadecanoyl)-4-hydroxy-L-prolin-(1-hexadecyl-ester | | 0.2 | | | | | |
| Citric Acid 10% solution | Citric Acid | | | | 1.3 | 1.6 | | |
| Colour (Symrise) | Colour | | | | | | 0.2 | |
| Colour I (Symrise) | Colour | | | | | | | 0.15 |
| Colour II (Symrise) | Colour | | | | | | | 0.35 |
| Crinipan AD (Symrise) | Climbazole | | | | | | 0.5 | |
| Crotein Q (Croda) | Hydroxypropyl Trimonium Hydrolyzed Collagen | | | 1.0 | | | | |
| Dehyquart A CA (Cognis) | Cetrimonium Chloride | 0.2 | 1.0 | | 4.0 | | | |
| Dehyquart SP (Cognis) | Quaternium-52 | | | 0.5 | | | | |
| Dehyton K (Cognis) | Cocamidopropyl Betaine | | 8.0 | | | | | 6.0 |
| D-Panthenol 75L (DSM Nutritional) | Panthenol | 0.5 | 1.0 | | 0.5 | | | |
| Dragocide Liquid (Symrise) | Phenoxyethanol, Methyl-, Ethyl-, Butyl-, Propyl-, Isobutylparaben | | 0.8 | 0.5 | | 0.5 | 0.7 | 0.8 |
| Dragoderm (Symrise) | Glycerin, Triticum Vulgare (Wheat) Gluten, Water (Aqua) | | 1.0 | | | | | 0.3 |
| Emulgin B2 (Cognis) | Ceteareth-20 | | | 0.7 | | | | |
| Ethanol 96% | Ethanol | 48.0 | | | 3.0 | 5.0 | | |
| Euperlan PK 771 (Cognis) | Glycol Distearate, Sodium Laureth Sulfate, Cocamide MEA, Laureth-10 | | | | | | 3.0 | |
| Euperlan PK 4000 (Cognis) | Glycol Distearate, Laureth-4, Cocoamidopropyl Betaine | | 2.5 | | | | | 1.0 |
| Extrapone Camomile (Symrise) | Water (Aqua), Propylene Glycol, Butylene Glycol, Chamomilla Recutita (Matricaria) Flower Extract, Glucose, Bisabolol | | | | | | 0.5 | |
| Extrapone Green Tea GW (Symrise) | Glycerin, Water (Aqua), Camellia Sinensis Leaf Extract | | | | | | 0.3 | |
| Extrapone Lemon grass (Symrise) | Propylene Glycol, Water (Aqua), PEG-40 Hydrogenated Castor Oil, Trideceth-9, Cymbopogon Citratus Leaf Oil, Lactic Acid | 0.4 | | | | | | 0.2 |
| Extrapone Rosemary GW (Symrise) | Glycerin, Water (Aqua), Rosmarinus officinalis (Rosemary) Leaf Extract | | 0.3 | | | | | |

TABLE 2-continued

| RAW MATERIAL NAME (SUPPLIER) | INCI | 12 | 13 | 14 | 15 | 16 | 17 | 18 |
|---|---|---|---|---|---|---|---|---|
| Fragrance (Symrise) | Fragrance | 0.5 | 0.3 | 0.4 | 0.2 | 0.4 | 0.5 | 0.3 |
| Frescolat ML (Symrise) | Menthyl Lactate | 0.5 | | | | 0.8 | 0.5 | |
| Glycerin, 99.5% | Glycerin | | | | | 10.0 | | |
| Hydrolite-5 (Symrise) | Pentylene Glycol | | | | 0.5 | | | |
| Lanette O (Cognis) | Cetearyl Alcohol | | | 2.5 | | | | |
| Luviskol K 30 (BASF) | PVP | | | | 2.0 | | | |
| Luviskol K 30 Powder (BASF) | PVP/Polyvinylpyrrolidone | | | | | 3.0 | | |
| Maygreen 1% solution in water (Symrise) | Maygreen, C.I. 47005, 61570 | 0.04 | | | | | | |
| Merquat 550 (Ondeo) | Polyquaterinium-7 | | 1.0 | | | | | 0.5 |
| Mulsifan RT 203/80 (Z&S) | C12-15 Pareth-12 | | | | | 4.0 | | |
| Neo Heliopan 357 (Symrise) | Butyl Methoxydibenzoylmethane | | | | 0.5 | | | |
| Neo Heliopan BB (Symrise) | Benzophenone-3 | 0.1 | 0.2 | | | | 0.3 | 0.2 |
| Neo Heliopan E 1000 (Symrise) | Isoamyl-p-methoxy-cinnamate | | | | 2.0 | | | |
| Neo-PCL Water soluble N (Symrise) | Trideceth-9, PEG-5 Ethylhexanoate, Water (Aqua) | | | | 1.0 | | | 1.0 |
| Neutrol TE (BASF) | Tetrahydroxypropyl Ethylendiamine | | | | | 1.4 | | |
| Niacinamide | Niacinamide | 0.2 | | | | | | |
| Polymer JR 400 (Nordmann, Rassmann) | Polyquaternium-10 | | | | | | 0.2 | |
| Potassium Sorbate | Potassium Sorbate | | | | 0.2 | | | |
| Rose CL forte (Symrise) | Water (Aqua), Glycerin, PEG-40 Hydrogenated Castor Oil, *Rosa Damascena* Flower Oil | | 0.5 | | | | | |
| Sodium Benzoate | Sodium Benzoate | | | | 0.5 | | | |
| Sodium Chloride | Sodium Chloride | | | 0.5 | | | 2.0 | 0.8 |
| Sodium Hydroxide, 10% sol. | Sodium Hydroxide | | | 0.1 | | | | |
| Solubilizer (Symrise) | PEG-40 Hydrogenated Castor Oil, Trideceth-9, Water (Aqua) | 1.0 | | | | | | |
| Tego Betain 810 (Evonic Goldschmidt) | Capryl/Capramidopropyl Betaine | | | | 0.5 | | | |
| Texapon K 14 S Special (Cognis) | Sodium Myreth Sulfate | | | | | | 12.0 | |
| Texapon N 70 (Cognis) | Sodium Laureth Sulfate | | | 10.0 | | | 12.0 | 35.0 |
| Water, demineralized | Wasser (Aqua) | Ad 100 | Ad 100 | Ad 100 | Ad 100 | Ad 100 | Ad 100 | Ad 100 |

Colour I: Food color quinoline yellow 70%
Colour II: Egg yellow C.I. 13015, 15510

Product Examples 19-31

Beauty from Inside

| Gelatine capsule for direct consumption | | | |
|---|---|---|---|
| | WEIGHT % | | |
| RAW MATERIAL NAME | 19 | 20 | 21 |
| Gelatine shell: | | | |
| Glycerin | 2.014 | 2.014 | 2.014 |
| Gelatine 240 Bloom | 7.91 | 7.91 | 7.91 |
| Sucralose | 0.065 | 0.065 | 0.065 |
| Allura Red | 0.006 | 0.006 | 0.006 |
| Brillant Blue | 0.005 | 0.005 | 0.005 |
| Core composition: | | | |
| Plant oil triglyceride (coconut oil fraktion) | Ad 100 | Ad 100 | Ad 100 |
| Aroma B | 9.95 | 12.0 | 12.0 |
| *Tetraselmis suecica* dry extract | | 0.005 | 0.01 |
| *Tetraselmis* extract (plant oil triglyceride:dry extract 95:5 (w/w) | 0.02 | | |

Aroma B had the following composition (figures in wt. %): 0.1% neotame powder, 0.05% aspartame, 29.3% peppermint oil arvensis, 29.3% peppermint oil piperita oil Willamette, 2.97% sucralose, 2.28% triacetin, 5.4% diethyl tartrate, 12.1% peppermint oil yakima, 0.7% ethanol, 3.36% 2-hydroxyethyl menthyl carbonate, 3.0% 2-hydroxypropyl menthyl carbonate, 0.27% vanillin, 5.5% D-limonene, 5.67% L-menthyl acetate.

The gelatine capsule suitable for direct consumption (produced in an analogous way to WO 2004/050069) had a diameter of 5 mm and the weight ratio of core material to shell material was 90:10. The capsule opened in the mouth in less than 10 seconds and dissolved completely in less than 50 seconds.

| Compressed tablets | | | |
|---|---|---|---|
| | WEIGHT % | | |
| RAW MATERIAL NAME | 22 | 23 | 24 |
| Magnesium stearate (as lubricant) | 0.9 | 0.9 | 0.9 |
| Citric acid | 0.2 | 0.2 | 0.2 |
| *Tetraselmis* dry extract | 0.01 | 0.005 | 0.001 |
| Dextrose | Ad 100 | Ad 100 | Ad 100 |

Preparation instructions: Mix all the constituents and press to a compressed product in a suitable machine.

| Chewing gums | | |
|---|---|---|
| | WEIGHT % | |
| RAW MATERIAL NAME | 25 | 26 |
| Chewing gum base | 21.0 | 30.0 |
| Glycerin | 0.5 | 1.0 |
| Menthol spearmint aroma | 1.0 | 0.7 |
| Glucose syrup | 16.5 | |
| Icing sugar | Ad 100 | |
| *Tetraselmis suecica* dry extract | | 0.01 |
| *Tetraselmis* extract (maltodextrin:dry extract 99:1 (w/w)) | 0.5 | |
| Sorbitol, powdered | | Ad 100 |
| Palatinite | | 9.5 |
| Xylitol | | 2.0 |
| Mannitol | | 3.0 |
| Aspartame | | 0.1 |
| Acesulfame K | | 0.1 |
| Emulgum/emulsifier | | 0.3 |
| Sorbitol 70%, in water | | 14.0 |

In Table 3 means

27=Instant beverage mix

28=Sugar-free instant beverage mix

29=Carbonated soft drink

30=Soja-fruit drink

31=Low-fat yoghurt

TABLE 3

| RAW MATERIAL NAME | WEIGHT % | | | | |
|---|---|---|---|---|---|
| | 27 | 28 | 29* | 30 | 31 |
| *Tetraselmis suecica* dry extract | | 0.005 | 0.007 | | 0.01 |
| *Tetraselmis* extract (maltodextrin:dry extract 95:5 (w/w)) | 0.2 | | | 0.02 | |
| Sugar (sucrose) | ad 100 | | | | |
| Citric acid | 4.00 | 33.33 | 0.2 | | |
| Trisodium citrate | 0.26 | | | | |
| Tricalcium phosphate | 0.22 | | | | |
| Ascorbic acid (vitamin C) | 0.24 | 0.44 | | | |
| Clouding agent and titanium dioxide (E 171) | 0.20 | | | | |
| Xanthan gum (E 415) | 0.072 | | | | |
| Sodium carboxy methyl cellulose (E 467) | 0.064 | | | | |
| Pectin (E 440) | 0.04 | | | | |
| Spray-dried pineapple flavor, including yellow colorant tartrazine | 0.40 | | | | |
| Spray-dried raspberry flavor, including red colorant | | 11.50 | | | |
| Lemon and lime flavor | | | 0.01 | | |

TABLE 3-continued

| RAW MATERIAL NAME | WEIGHT % | | | | |
|---|---|---|---|---|---|
| | 27 | 28 | 29* | 30 | 31 |
| D-Limonene | | | 0.005 | | |
| Maltodextrin (powder) | | ad 100 | | | |
| Aspartame | | 3.30 | | | |
| Saccharose | | | 8.0 | 6.0 | 5.0 |
| Hesperetin (1 wt. % in 1,2-propylene glycol) | | | 0.05 | | |
| Phloretin (1 wt. % in 1,2-propylene glycol) | | | 0.05 | | |
| Ethylhydroxymethylfuranone | | | 0.01 ppb | | |
| Vanilla flavor | | | | 0.10 | 0.125 |
| Vanillin | | | 15 ppb | | |
| Maltol | | | 350 ppb | | |
| 2,5-Dimethyl-4-hydroxy-2H-furan-3-one | | | 3 ppb | | |
| 1,2-Propylene glycol | | | 0.1 | | |
| Mixture of fruit juice concentrates | | | | 45.0 | |
| Soja powder | | | | 5.0 | |
| Yoghurt (1.5 wt. % fat) | | | | ad 100 | |
| Water | | | ad 100 | | ad 100 |

*Carbonated after filling into bottles.

The invention claimed is:

1. A method for inhibiting the growth of human hair comprising applying to a human, a cosmetic, dermatological, or therapeutic product comprising an extract of Tetraselmis sp. in an amount effective for inhibiting the growth of human hair.

2. The method according to claim 1, wherein the Tetraselmis sp. is Tetraselmis suecica.

3. The method of claim 1, wherein the extract of Tetraselmis sp. is obtained by extracting viable, freeze-dried or dried cells of Tetraselmis sp., with a liquid extractant selected from the group consisting of hexane, ethyl acetate, ethanol, water, methanol, isopropanol and mixtures of two or more of these extractants, and optionally adjusting the phototoxicity of the composition to a phototoxicity index of less than 5.

4. A method for inhibiting the growth of human hair comprising applying an extract of Tetraselmis suecica, wherein the extract is obtainable or obtained by a method according to claim 3.

5. The method according to claim 3, wherein for adjusting the phototoxicity the extract is treated with activated carbon in a ratio dry extract:activated carbon of 3:1 to 1:30 all weights given as dry weights.

6. The method according to claim 5, wherein the ratio of dry extract:activated carbon is 1:1 to 1:15.

7. The method according to claim 1, wherein the extraction comprises a) exposition of the cell material to the extractant for up to 24 hours at a temperature of not more than 50° C., and b) removal of the cell material to obtain an extract, the extract being the composition or being further processed into the composition.

8. The method according to claim 7, wherein the extraction comprises repeating steps a) and b) once, twice, three or four times, and wherein in each step a) the cell material removed in the respective prior step b) is used, and the extracts of steps b) are combined.

9. The method according to claim 7, wherein the cell material used in the first step a) is freeze dried Tetraselmis sp.

10. The method according to claim 7, wherein for extraction cell material is obtained in step b) of a prior extraction with a different extractant.

11. The method according to claim 5, wherein the Tetraselmis sp. is Tetraselmis suecica.

12. The method according to claim 6, wherein the Tetraselmis sp. is Tetraselmis suecica.

13. The method according to claim 9, wherein the Tetraselmis sp. is Tetraselmis suecica.

14. The method according to claim 2, wherein the extraction comprises a) exposition of the cell material to the extractant for up to 24 hours at a temperature of not more than 50° C., and b) removal of the cell material to obtain an extract, the extract being the composition or being further processed into the composition.

15. The method according to claim 14, wherein the extraction comprises repeating steps a) and b) once, twice, three or four times, and wherein in each step a) the cell material removed in the respective prior step b) is used, and the extracts of steps b) are combined.

16. The method according to claim 14, wherein for extraction cell material is obtained in step b) of a prior extraction with a different extractant.

17. The method of claim 3, wherein the cells of Tetraselmis sp. are
first extracted with ethyl acetate,
then extracted with ethanol,
then extracted with water or ethyl acetate, and
then extracted with 30% ethanol or water.

18. The method of claim 3, wherein the cells of Tetraselmis sp. are extracted with methanol, ethanol or isopropyl alcohol, followed by extraction with water.

19. The method of claim 3, wherein the cells of Tetraselmis sp. are
first extracted with hexane,
then extracted with ethyl acetate,
then extracted with ethanol, and
then extracted with water.

20. The method of claim 3, wherein the cells of Tetraselmis sp. are
first extracted with hexane, ethyl acetate, methanol or ethanol,
then extracted with hexane or 30% ethanol,
then extracted with ethyl acetate, and
then extracted with ethanol.

21. The method of claim 3, wherein the liquid extractant comprises a mixture of at least two of the enumerated extractants.

* * * * *